(12) United States Patent
Choi

(10) Patent No.: US 10,422,761 B2
(45) Date of Patent: Sep. 24, 2019

(54) THREE DIMENSIONAL ELECTRICAL IMPEDANCE TOMOGRAPHIC METHOD

(71) Applicant: NATIONAL CHIAO TUNG UNIVERSITY, Hsinchu (TW)

(72) Inventor: Charles Tak Ming Choi, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 0 days.

(21) Appl. No.: 15/158,306

(22) Filed: May 18, 2016

(65) Prior Publication Data
US 2016/0341684 A1 Nov. 24, 2016

(30) Foreign Application Priority Data

May 18, 2015 (TW) .............................. 104115807 A

(51) Int. Cl.
*G01N 27/02* (2006.01)
*A61B 5/00* (2006.01)
*A61B 5/053* (2006.01)

(52) U.S. Cl.
CPC ............ *G01N 27/02* (2013.01); *A61B 5/0042* (2013.01); *A61B 5/0536* (2013.01); *A61B 5/0538* (2013.01); *A61B 5/6814* (2013.01); *A61B 2560/0468* (2013.01); *A61B 2562/046* (2013.01)

(58) Field of Classification Search
CPC .... G01N 27/02; A61B 5/0042; A61B 5/0536; A61B 5/6814; A61B 5/0538; A61B 2562/046; A61B 2560/0468
See application file for complete search history.

(56) References Cited

U.S. PATENT DOCUMENTS 6,725,087 B1   4/2004 Rubinsky et al.
8,768,018 B2 * 7/2014 Ishikawa ............... G06T 3/0093
                                                   382/128
(Continued)

FOREIGN PATENT DOCUMENTS

CN    102973269 A    3/2013
CN    104055515 A    9/2014

OTHER PUBLICATIONS

Halter, Ryan J., "A Broadband High-Frequency Electrical Impedance Tomography System for Breast Imaging," IEEE Transactions on Biomedical Engineering, Vo. 55, No. 2, Feb. 2008, pp. 650-659.

*Primary Examiner* — Akm Zakaria
(74) *Attorney, Agent, or Firm* — Muncy, Geissler, Olds & Lowe, P.C.

(57) ABSTRACT

A three dimensional electrical impedance tomographic method is disclosed. The three dimensional electrical impedance tomographic method includes steps of disposing an implantation body, wherein an electrode array formed by a plurality of electrodes is disposed on the implantation body; disposing an electrode controller to control any electrode in the electrode array; generating more independent voltage data measured on the plurality of electrodes on the same curve surface by combining current control technology or virtual electrode technology; and performing a calculation to convert the plurality of horizontal or vertical voltage data into a three dimensional electrical impedance tomographic image.

6 Claims, 34 Drawing Sheets

(56) References Cited

U.S. PATENT DOCUMENTS

| | | | |
|---|---|---|---|
| 2005/0083265 A1* | 4/2005 | Joo | G09G 3/2944 |
| | | | 345/63 |
| 2011/0082383 A1* | 4/2011 | Cory | A61B 5/0536 |
| | | | 600/547 |
| 2011/0163770 A1* | 7/2011 | Mahalingam | G01N 33/2823 |
| | | | 324/693 |
| 2013/0231547 A1* | 9/2013 | Kim | A61B 5/0532 |
| | | | 600/393 |
| 2014/0039341 A1* | 2/2014 | Bohorquez | A61B 5/0537 |
| | | | 600/547 |
| 2016/0022165 A1* | 1/2016 | Sackellares | A61B 5/0478 |
| | | | 600/383 |
| 2016/0030751 A1* | 2/2016 | Ghosh | A61B 5/04085 |
| | | | 607/18 |

* cited by examiner

```
┌─────────────────────────────────────────────────────────────────────┐
│ An implantation body is disposed in an object to be imaged and the  │──S1
│ implantation body has a bearing surface                             │
└─────────────────────────────────────────────────────────────────────┘
                                    ↓
┌─────────────────────────────────────────────────────────────────────┐
│ An electrode array is disposed on the bearing surface. The electrode│──S2
│ array has a plurality of electrodes                                 │
└─────────────────────────────────────────────────────────────────────┘
                                    ↓
┌─────────────────────────────────────────────────────────────────────┐
│ An electrode controller is disposed. The electrode controller is    │──S3
│ electrically connected to the plurality of electrodes respectively  │
└─────────────────────────────────────────────────────────────────────┘
                                    ↓
┌─────────────────────────────────────────────────────────────────────┐
│ The plurality of electrodes located at the same horizontal plane on │
│ the electrode array are defined as a horizontal electrode set. The  │──S4
│ electrode array may include a plurality of horizontal electrode sets│
└─────────────────────────────────────────────────────────────────────┘
                                    ↓
┌─────────────────────────────────────────────────────────────────────┐
│ A plurality of horizontal control signals are generated. The        │──S5
│ plurality of horizontal control signals include a horizontal        │
│ selection parameter respectively                                    │
└─────────────────────────────────────────────────────────────────────┘
                                    ↓
┌─────────────────────────────────────────────────────────────────────┐
│ One of the plurality of horizontal control signals is received      │
│ through the electrode controller. Any horizontal electrode set is   │
│ selected by the electrode controller according to the horizontal    │──S6
│ selection parameter of the horizontal control signal and then a     │
│ plurality of horizontal driving electrodes are selected from the    │
│ selected horizontal electrode set                                   │
└─────────────────────────────────────────────────────────────────────┘
                                    ↓
┌─────────────────────────────────────────────────────────────────────┐
│ When the electrode controller drives the plurality of horizontal    │
│ driving electrodes, all other electrodes except the plurality of    │
│ horizontal driving electrodes in the selected horizontal electrode  │──S7
│ sets are used to receive signals transmitted by the plurality of    │
│ horizontal driving electrodes in order to form a set of horizontal  │
│ voltage data                                                        │
└─────────────────────────────────────────────────────────────────────┘
                                    ↓
┌─────────────────────────────────────────────────────────────────────┐
│ He plurality of electrodes located at the same vertical plane on the│
│ electrode array are defined as a vertical electrode set. The        │──S8
│ electrode array may include a plurality of vertical electrode sets  │
└─────────────────────────────────────────────────────────────────────┘
                                    ↓
┌─────────────────────────────────────────────────────────────────────┐
│ A plurality of vertical control signals are generated. The plurality│──S9
│ of vertical control signals include a vertical selection parameter  │
│ respectively                                                        │
└─────────────────────────────────────────────────────────────────────┘
                                    ↓
┌─────────────────────────────────────────────────────────────────────┐
│ One of the plurality of vertical control signals is received through│
│ the electrode controller. Any vertical electrode set is selected by │
│ the electrode controller according to the vertical selection        │──S10
│ parameter of the vertical control signal and then a plurality of    │
│ vertical driving electrodes are selected from the selected vertical │
│ electrode set                                                       │
└─────────────────────────────────────────────────────────────────────┘
                                    ↓
┌─────────────────────────────────────────────────────────────────────┐
│ When the electrode controller drives the plurality of vertical      │
│ driving electrodes, all other electrodes except the plurality of    │
│ vertical driving electrodes in the selected vertical electrode sets │──S11
│ are used to receive signals transmitted by the plurality of vertical│
│ driving electrodes in order to form a set of vertical voltage data  │
└─────────────────────────────────────────────────────────────────────┘
                                    ↓
┌─────────────────────────────────────────────────────────────────────┐
│ A solver, such as a linear solver or nonlinear solver is performed  │
│ to combine the plurality of horizontal control signals, the         │
│ plurality of sets of horizontal voltage data, the plurality of      │──S12
│ vertical control signals and the plurality of sets of vertical      │
│ voltage data in order to form the three dimensional electrical      │
│ impedance tomographic images                                        │
└─────────────────────────────────────────────────────────────────────┘
```

FIG. 7

```
┌─────────────────────────────────────────────────────────────────┐
│ An implantation body is disposed in an object to be imaged and the │
│ implantation body has a bearing surface. The shape of the bearing surface │──S21
│ may be spherical, cylindrical, or irregular shaped object like a head or │
│ abdomen of a human body                                         │
└─────────────────────────────────────────────────────────────────┘
                                  ↓
┌─────────────────────────────────────────────────────────────────┐
│ An electrode array is disposed on the bearing surface. The electrode │──S22
│ array has a plurality of electrodes                             │
└─────────────────────────────────────────────────────────────────┘
                                  ↓
┌─────────────────────────────────────────────────────────────────┐
│ An electrode controller is disposed. The electrode controller is │──S23
│ electrically connected to the plurality of electrodes respectively │
└─────────────────────────────────────────────────────────────────┘
                                  ↓
┌─────────────────────────────────────────────────────────────────┐
│ The plurality of electrodes located at the same plane on the electrode │
│ array are defined as a plane electrode set. The electrode array may │──S24
│ include a plurality of plane electrode sets. For implementation, the plane │
│ may be a horizontal plane, a vertical plane or an inclined plane with angle │
└─────────────────────────────────────────────────────────────────┘
                                  ↓
┌─────────────────────────────────────────────────────────────────┐
│ A plurality of plane control signals are generated. The plurality of plane │
│ control signals include a plane selection parameter and a plane power │──S25
│ control parameter respectively                                  │
└─────────────────────────────────────────────────────────────────┘
                                  ↓
┌─────────────────────────────────────────────────────────────────┐
│ The plurality of plane control signals are received through the electrode │
│ controller respectively. Any plane electrode set is selected by the │
│ electrode controller according to the plane selection parameter of the │──S26
│ plane control signal and then a plurality of plane driving electrodes are │
│ selected from the selected plane electrode set                  │
└─────────────────────────────────────────────────────────────────┘
                                  ↓
┌─────────────────────────────────────────────────────────────────┐
│ Power output ratios of any electrode in the plurality of plane driving │
│ electrodes are respectively controlled by the plane power control │──S27
│ parameter and a first distribution condition                    │
└─────────────────────────────────────────────────────────────────┘
                                  ↓
┌─────────────────────────────────────────────────────────────────┐
│ When the electrode controller drives the plurality of plane driving │
│ electrodes, all other electrodes except the plurality of plane driving │
│ electrodes in the selected plane electrode sets are used to receive signals │──S28
│ transmitted by the plurality of plane driving electrodes in order to form a │
│ set of plane voltage data                                       │
└─────────────────────────────────────────────────────────────────┘
                                  ↓
┌─────────────────────────────────────────────────────────────────┐
│ A calculation is performed to combine the plurality of plane control │
│ signals and the plurality of sets of plane voltage data in order to form a │──S29
│ three dimensional electrical impedance tomographic image        │
│ corresponding to the object to be imaged                        │
└─────────────────────────────────────────────────────────────────┘
```

FIG. 8

THREE DIMENSIONAL ELECTRICAL IMPEDANCE TOMOGRAPHIC METHOD

CROSS-REFERENCE TO RELATED APPLICATION

This application claims priority from Taiwan Patent Application No. 104115807, filed on May 18, 2015, in the Taiwan Intellectual Property Office, the content of which are hereby incorporated by reference in their entirety for all purposes.

BACKGROUND OF THE INVENTION

1. Field of the Invention

The present invention relates to an electrical impedance tomographic method, in particular to a three dimensional electrical impedance tomographic method.

2. Description of the Related Art

The electrical impedance tomography (EIT) is a medical imaging technology which produces tomographic images by measuring the conductivity distribution of a certain part of human body. It is currently applied to perform photography for the internal structure of biological organization. Compared to the other conventional imaging technologies such as positron emission tomography (PET), computed tomography (CT) and magnetic resonance imaging (MRI), the EIT is a tomography technology with inexpensive price, non-invasive property and without ionizing radiation. However, the disadvantage of the EIT is that the resolution of the images produced are relatively low (when compare with CT or MRI) because it is limited by the number of electrodes which acquire the measurement data. On the other hand, having too many numbers of electrodes could reduce the signal to noise ratio of the measurement data which means poor quality of data. A general EIT image reconstruction method controls the input of a current to an object through a set of electrodes and measures the voltage values produced between the other electrodes which were not being used for inputting current into the object. Next, current is again injected into the object using a different set of electrodes, and voltage values produced between the other electrodes (which were not being used for inputting current) are measured. This is repeated until all the electrodes have been used as inputting electrodes. The measured voltages of all the measurement (this is the measurement data as discussed above) are collectively being used to reconstruct a three dimensional EIT image.

The principle of the EIT is to place the conductive electrode on the surface of the object to be imaged. Then, a small amount of alternating current is applied to some or all of the electrodes and the potential difference produced is measured by the electrodes. The data of surface electrical measurement may thus be achieved and the electrical conductivity and permittivity distribution of a part of an object to be measured may be analyzed based on the data. In the conventional technique, the U.S. Pat. No. 6,725,087 has already disclosed an element for data acquisition, processing and imaging element system connected through a communication network, and thus allowing the function of data acquisition, processing and imaging to be executed at different positions of the network. In addition, the broadband frequency of the EIT system operation ranging from 10 KHz to 10 MHz has been disclosed in the paper "A broadband high-frequency electrical impedance tomography system for breast imaging". Although the precision of impedance measurement may be increased by increasing the frequency range of current, the resolution of the EIT system still has not been improved.

The EIT is applicable to the reconstruction the impedance distribution of an object. However, the resolution of the EIT is limited by the number and size of the electrodes. Therefore, an EIT technology with high resolution and more complete three dimensional information is urgently needed at present.

SUMMARY OF THE INVENTION

In view of the disadvantages of the conventional techniques, the objective of the present invention is to provide a three dimensional electrical impedance tomographic method to solve the problem of insufficient resolution of the conventional electrical impedance tomographic method.

Another objective of the present invention is to provide a three dimensional electrical impedance tomographic method, which executes the systematization at the beginning of the measurement to produce vertical and horizontal images, then transmits and detects the horizontal and vertical detection signals. The received signals are directly combined into three dimensional signals and thus a better measurement result is produced.

Another objective of the present invention is to provide a three dimensional electrical impedance tomographic method, which may produce vertical and horizontal images to effectively enhance the application of tomographic images.

Based on the objectives described above, the present invention provides a three dimensional electrical impedance tomographic method, which is used to form a three dimensional electrical impedance tomographic image corresponding to an object to be imaged. The method includes the following steps: providing an electrode array which has a plurality of electrodes and the electrode array may locate at an inner section or an outer section of an object to be imaged; disposing an electrode controller and the electrode controller is electrically connected to the plurality of electrodes respectively; defining the plurality of electrodes located at the same horizontal plane on the electrode array as a horizontal electrode set and the electrode array may include a plurality of horizontal electrode sets; generating a plurality of horizontal control signals and the plurality of horizontal control signals include a horizontal selection parameter respectively; receiving one of the plurality of horizontal control signals respectively through the electrode controller, selecting any horizontal electrode set by the electrode controller according to the horizontal selection parameter of the horizontal control signal and then selecting a plurality of horizontal driving electrodes from the selected horizontal electrode set; when the electrode controller drives the plurality of horizontal driving electrodes, using all other electrodes except the plurality of horizontal driving electrodes in the selected horizontal electrode sets to receive signals transmitted by the plurality of horizontal driving electrodes in order to form a set of horizontal voltage data; defining the plurality of electrodes located at the same vertical plane on the electrode array as a vertical electrode set and the electrode array may include a plurality of vertical electrode sets; generating a plurality of vertical control signals and the plurality of vertical control signals include a vertical selection parameter respectively; receiving one of the plurality of vertical control signals respectively through the electrode controller, selecting any vertical electrode set by the electrode controller according to the vertical selection parameter of the vertical control signal, and then selecting a plurality of vertical driving electrodes from the selected vertical electrode sets; when the electrode controller drives the plurality of vertical driving electrodes, using all other electrodes except the plurality of vertical driving electrodes in the selected vertical electrode sets to receive signals transmitted by the plurality of vertical driving electrodes in order to form a set of vertical voltage data; and performing a calculation to combine the plurality of horizontal control signals, the plurality of sets of horizontal voltage data, the plurality of vertical control signals and the plurality of sets of vertical voltage data in order to form the three dimensional electrical impedance tomographic images.

Preferably, the electrode array is disposed on a surface of implantation body, and the implantation body is placed inside the object to be imaged; or the electrode array is disposed on an inner surface of a cover body, the object to be imaged is wrapped around by the cover body.

Preferably, the plurality of horizontal control signals further include a horizontal power control parameter respectively, wherein the electrode controller respectively controls a power output ratio of any electrode in the plurality of horizontal driving electrodes by the horizontal power control parameter and a first distribution condition. The plurality of vertical control signals further include a vertical power control parameter respectively, wherein the electrode controller respectively controls a power output ratio of any electrode in the plurality of vertical driving electrodes by the vertical power control parameter and a second distribution condition.

Preferably, a plurality of horizontal control signals and a plurality of vertical control signals may be a current signal.

Preferably, the first distribution condition is that a current distribution is performed according to the horizontal power control parameter, and a sum of current of the plurality of horizontal driving electrodes is made to be zero. The second distribution condition is that the current distribution is performed according to the vertical power control parameter, and a sum of current of the plurality of vertical driving electrodes is made to be zero.

Based on the objectives described above, the present invention provides a three dimensional electrical impedance tomographic method, which is used to form a three dimensional electrical impedance tomographic image corresponding to an object to be imaged. The method includes the following steps: providing an electrode array which has a plurality of electrodes and the electrode array may locate at an inner section or an outer section of an object to be imaged; disposing an electrode controller and the electrode controller is electrically connected to the plurality of electrodes respectively; defining the plurality of electrodes located at the same plane on the electrode array as a plane electrode set and the electrode array may include a plurality of plane electrode sets; generating a plurality of plane control signals and the plurality of plane control signals include a plane selection parameter and a plane power control parameter respectively; receiving the plurality of plane control signals respectively through the electrode controller, selecting any plane electrode set by the electrode controller according to the plane selection parameter of the plane control signal, and then selecting a plurality of plane driving electrodes from the selected plane electrode set; controlling a power output ratio of any electrode in the plurality of plane driving electrodes respectively by the plane power control parameter and a first distribution condition; when the electrode controller drives the plurality of plane driving electrodes, using all other electrodes except the plurality of plane driving electrodes in the selected plane electrode sets to receive signals transmitted by the plurality of plane driving electrodes in order to form a set of plane voltage data; and performing a calculation to combine the plurality of plane control signals and the plurality of sets of plane voltage data in order to form the three dimensional electrical impedance tomographic images.

Preferably, the plurality of electrodes are located on a surface of implantation body, and the implantation body is placed inside the object to be imaged.

Preferably, the plurality of electrodes are located on an inner surface of a chamber, and the object to be imaged is located inside the chamber.

Preferably, the plurality of electrodes are located on an inner surface of clothes, and the object to be imaged is located inside the clothes.

Preferably, the plurality of electrodes are located on an inner surface of a cap or a hat, and the object to be imaged is located inside the cap or the hat.

Wherein, the plane control signal may be a current signal.

Preferably, the first distribution condition is that a current distribution is performed according to the plane power control parameter, and a sum of current of the plurality of plane driving electrodes is made to be zero.

Based on the objectives described above, the present invention provides a three dimensional electrical impedance tomographic method, which is used to form a three dimensional electrical impedance tomographic image corresponding to an object to be imaged. The application of three dimensional electrical impedance tomographic method includes the following steps: providing a plurality of electrodes, wherein the plurality of electrodes are located at an inner section or an outer section of the object to be imaged, the plurality of electrodes are not disposed on the same plane; disposing an electrode controller, the electrode controller electrically connected to the plurality of electrodes respectively; defining at least two electrodes selected from the plurality of electrodes as a driving electrode set; generating a plurality of control signals, the plurality of control signals comprising a selection parameter respectively; when the electrode controller receives one of the plurality of control signals respectively to drives the plurality of driving electrodes, using all other electrodes except the plurality of driving electrodes in the selected electrode sets to receive signals transmitted by the plurality of driving electrodes in order to form a set of voltage data; and performing a calculation and forming the three dimensional electrical impedance tomographic images according to the plurality of control signals and the plurality of sets of voltage data.

In order to facilitate further comprehension and understanding of the technical features and the achieved effects of the present invention, it will be illustrated as follows with reference to the preferred embodiments and the detailed descriptions.

BRIEF DESCRIPTION OF THE DRAWINGS

The above and other features and the advantages of the present invention will become more apparent by illustrating the exemplary embodiments thereof in details with reference to the accompanying drawings, wherein:

FIG. 7 is a flowchart according to the third embodiment of the three dimensional electrical impedance tomographic method of the present invention;

FIG. 8 is a flowchart according to the fourth embodiment of the three dimensional electrical impedance tomographic method of the present invention;

DETAILED DESCRIPTION OF THE PREFERRED EMBODIMENTS

As used herein, the words "and/or" include any or all combinations of one or more relevant listed items. When the description of "at least one" is prefixed in front of a list of elements, it modifies the entire list of elements rather than individual element in the list.

Figure 1:
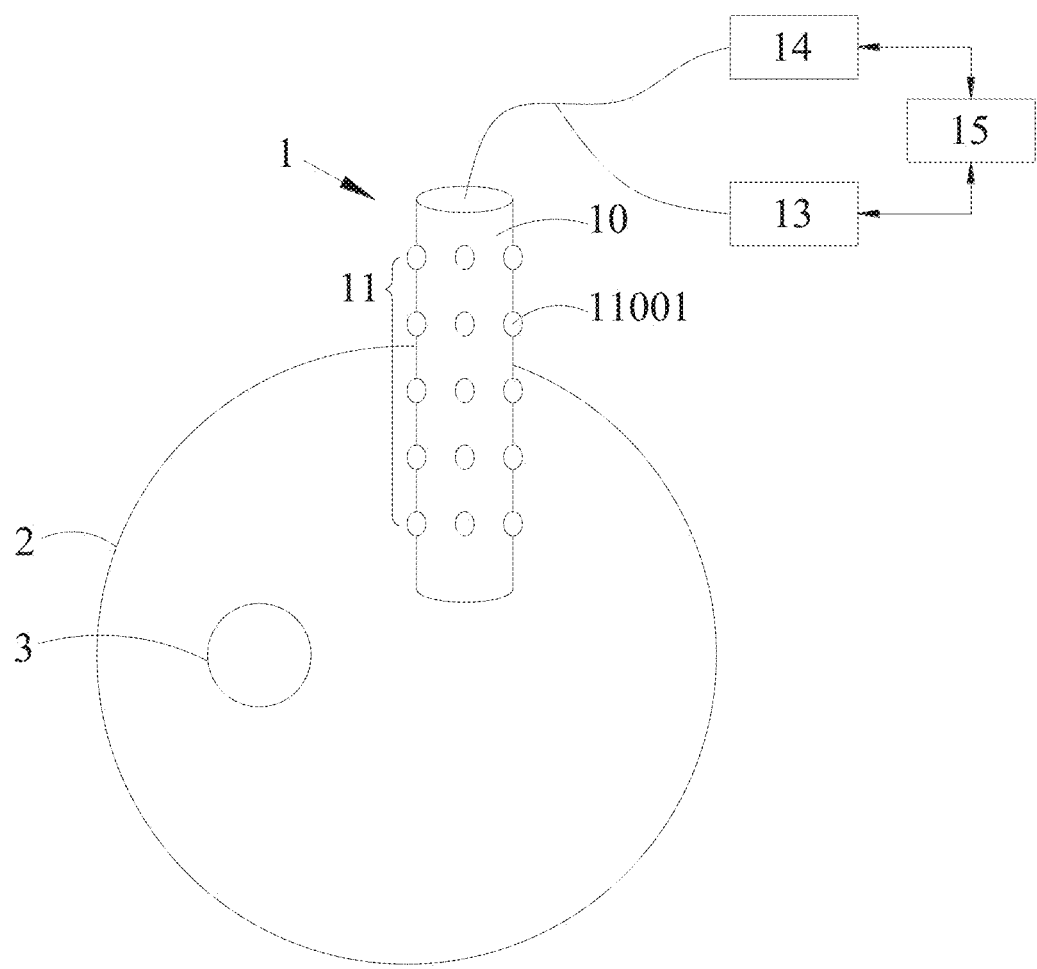
FIG. 1 is a schematic diagram of the device according to the first embodiment of the three dimensional electrical impedance tomographic method of the present invention.

Please refer to FIG. 1, which is a schematic diagram of the device according to the first embodiment of the three dimensional electrical impedance tomographic method of the present invention. In the first embodiment, a probe-shape implantation body 1 is implanted in an object 2, which is to be imaged. The implantation body 1 has a cylindrical bearing surface 10. An electrode array 11 consists of a plurality of electrodes 11001 is mounted on the bearing surface 10. The first embodiment takes outward-looking as an example. It should be noted that the bearing surface 10 is taken as an example only for convenience of illustration. In the practical application, however, the electrode may also be directly disposed on the implantation body.

Electrode controllers 13 are disposed outside the implantation body 1. The electrode controllers 13 are electrically connected to a plurality of electrodes 11001 respectively to perform the driving of the electrodes 11001. A data acquisition device 14 is further disposed outside the implantation body 1 in order to collect and analyze detection signals of the electrodes 11001. The electrode controllers 13 and data acquisition device 14 are respectively connected to a computing device 15. The computing device 15 may be a personal computer, a work station or a cloud server, which is used to collect the measured data and to reconstruct a three dimensional EIT image. After obtaining the three dimensional EIT image, the result can be display by the monitor or the display panel of the computing device 15. A target 3, which has a different impedance value from the object 2, has been formed in the object 2, which is to be imaged by the electrical impedance tomography system. Target 3 is the object which is intended to be detected and identified by the three dimensional electrical impedance tomographic method of the present invention.

Figure 2:
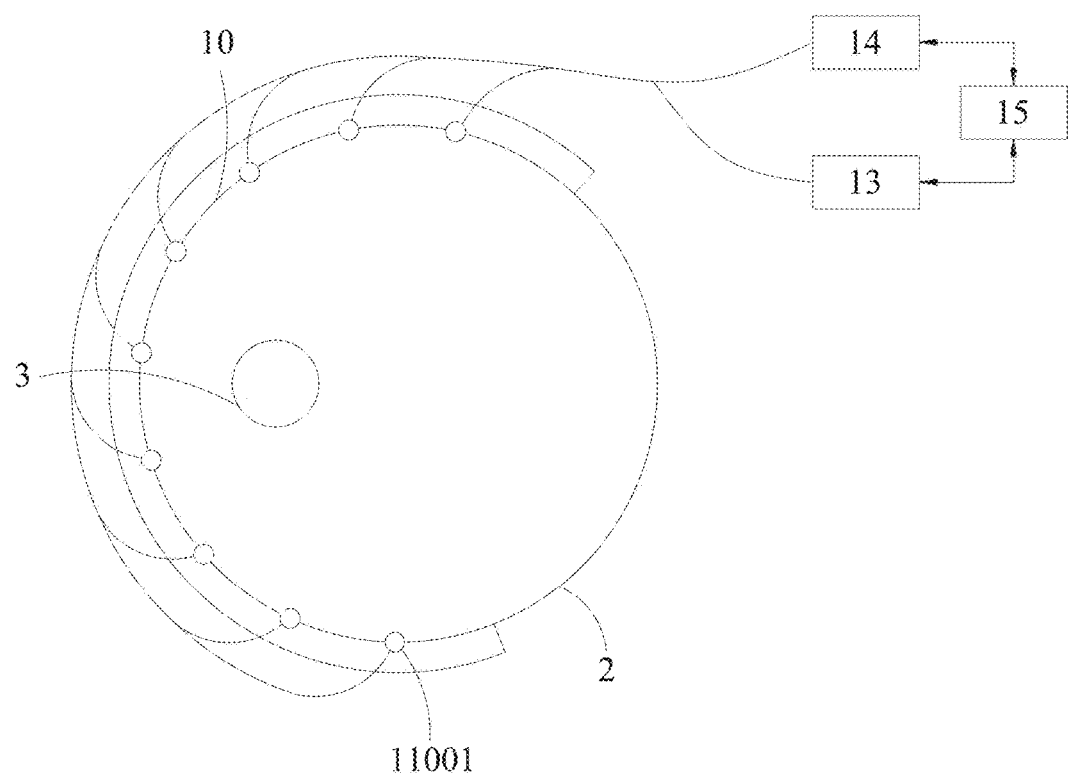
FIG. 2 is a top view of the device according to the second embodiment of the three dimensional electrical impedance tomographic method of the present invention.

Please refer to FIG. 2, which is a top view of the device according to the second embodiment of the three dimensional electrical impedance tomographic method of the present invention. Wherein the part as same as FIG. 1 is not repeated. In the second embodiment, the surface 10 is a three dimensional curve surface and covers the object 2, which is to be imaged. Thus, the plurality of electrodes 11001 are attached to the surface of the object 2, which is to be imaged, by wrapping around it externally. Target 3 is detected within the object item 2. The second embodiment takes inward-looking as an example.

For implementation, the plurality of electrodes 11001 may be disposed on an inner surface of a cover body. The cover body is used to cover the object to be imaged. For example, the cover body may be a large detection unit or chamber which may cover the torso of a human body; or the cover body may be a small detection cover which is, for example, used to cover the head of patient (like in an EEG cap or hat) as shown in FIG. 10A, FIG. 10B, FIG. 11A and FIG. 11B; or the cover body may be a belt-shape detection device which wraps around the abdomen or thorax of a human body; or the cover body may be clothes which wear by the patient (like dress, vests, shirts).

Figure 3A:
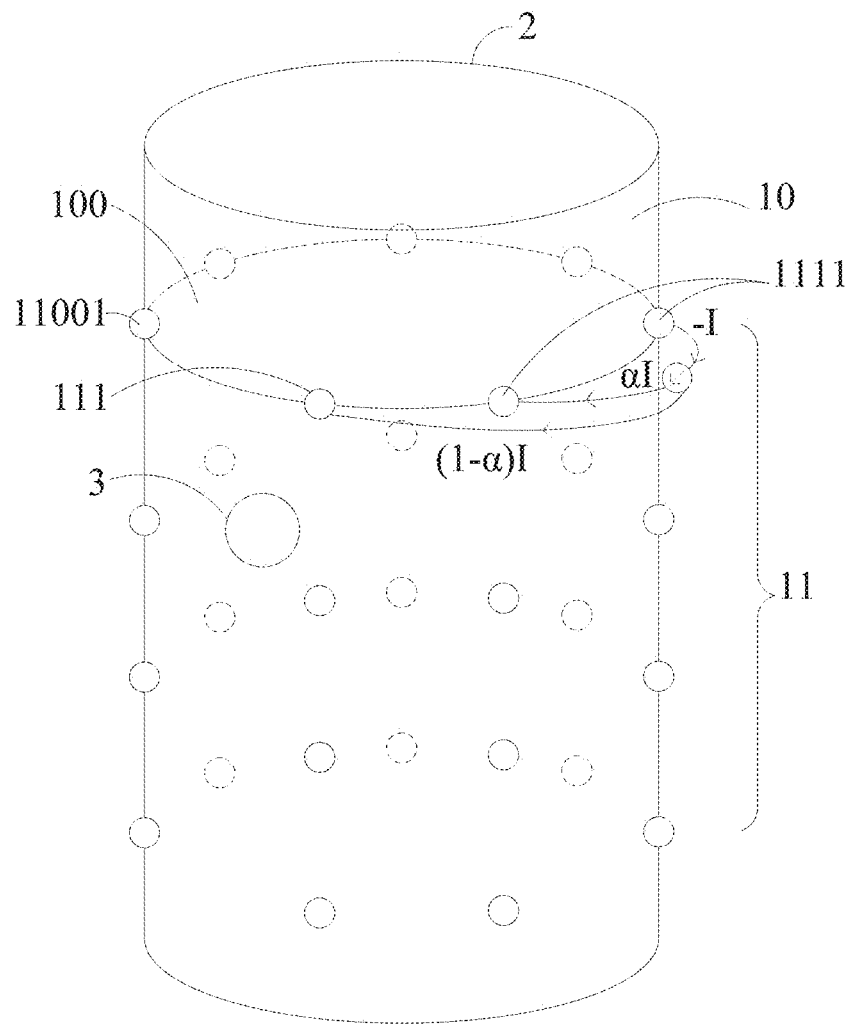
FIG. 3A is a schematic diagram of the horizontal plane according to the third embodiment of the three dimensional electrical impedance tomographic method of the present invention.
Figure 3B:
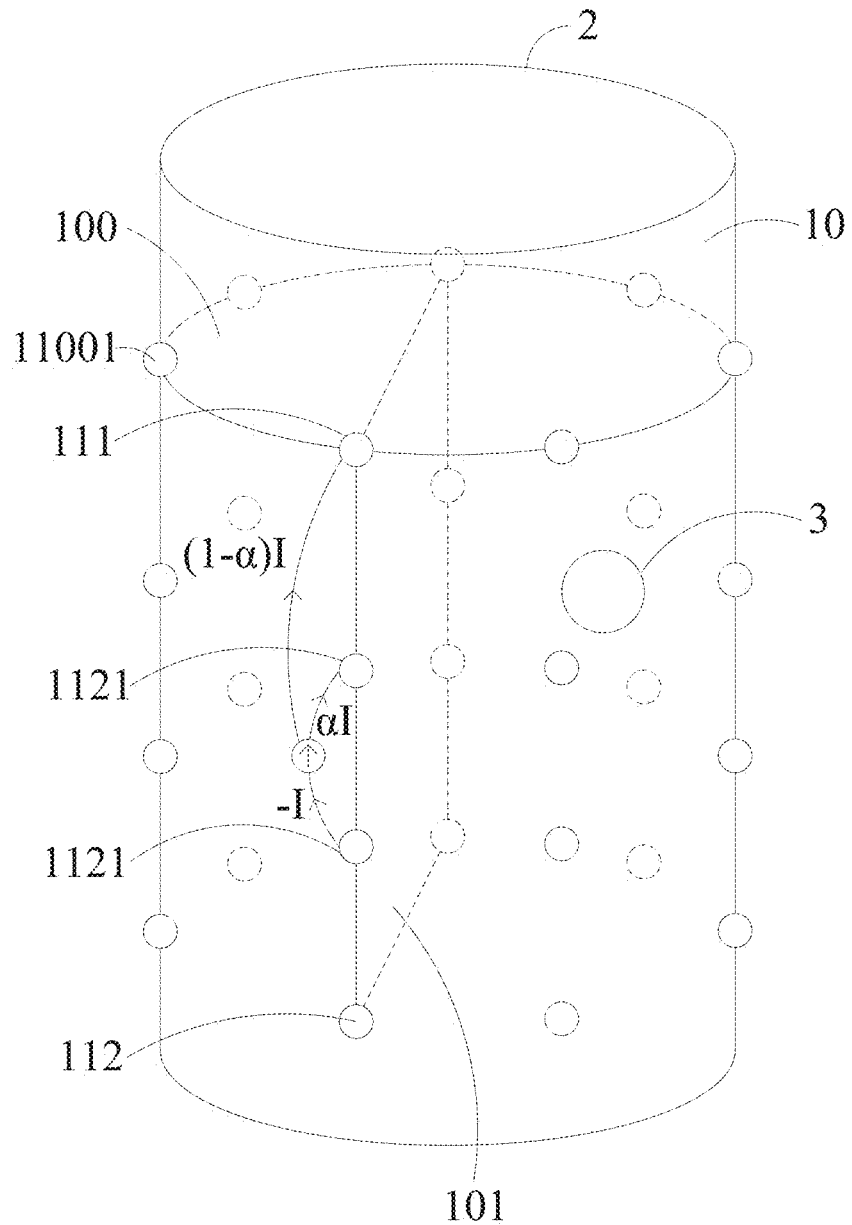
FIG. 3B is a schematic diagram of the vertical plane according to the third embodiment of the three dimensional electrical impedance tomographic method of the present invention.
Figure 3C:
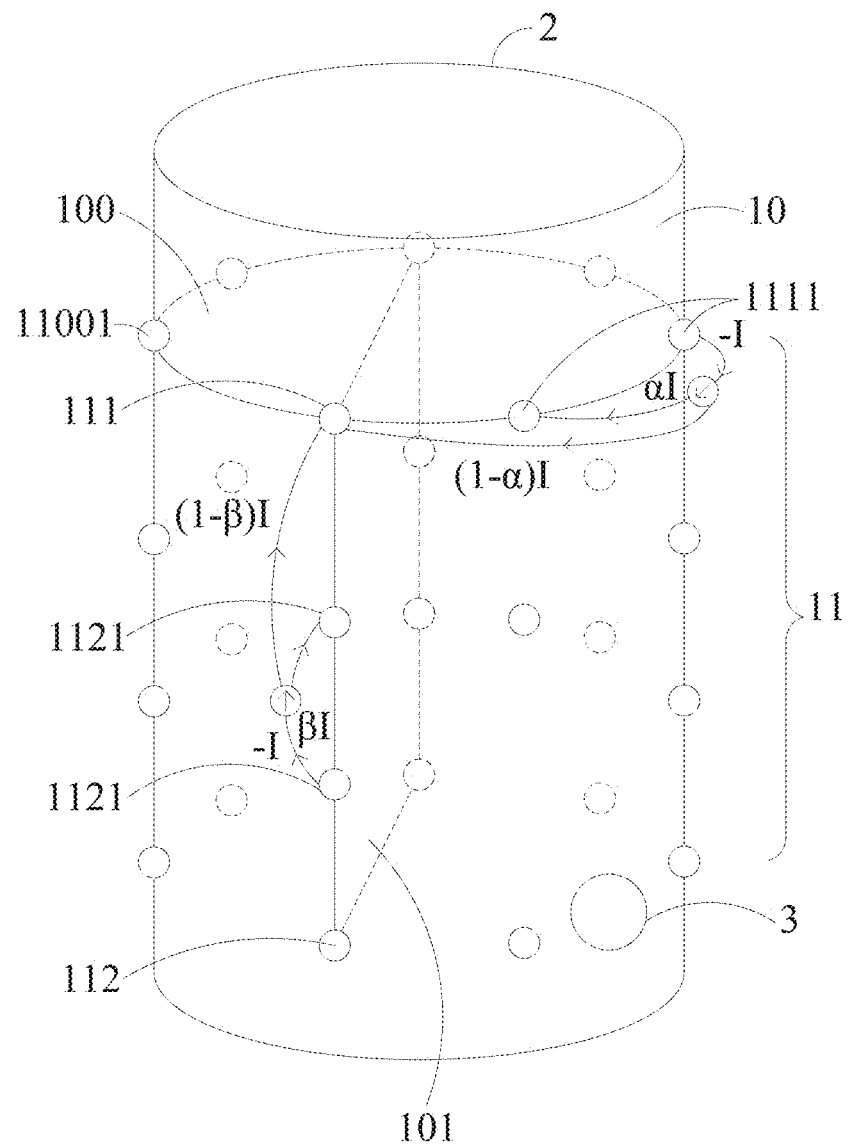
FIG. 3C is a schematic diagram of using the horizontal and vertical plane at the same time according to the third embodiment of the three dimensional electrical impedance tomographic method of the present invention.

Please refer to FIG. 3A, FIG. 3B and FIG. 3C, which are a schematic diagram of the horizontal plane, a schematic diagram of the vertical plane and a schematic diagram of using the horizontal and vertical planes at the same time respectively according to the third embodiment of the three dimensional electrical impedance tomographic method of the present invention, and takes the inward-looking as an example. The top view thereof is as same as FIG. 2.

In FIG. 3A, the plurality of electrodes 11001 located at the same horizontal plane 100 in the electrode array 11 are defined as a horizontal electrode set 111 and then a plurality of electrodes 11001 are selected from the horizontal electrode set 111 to be horizontal driving electrodes 1111. Next, a small amount of alternating current I is inputted from one of the plurality of horizontal driving electrodes 1111, and the other two horizontal driving electrodes 1111 output the alternating current $\alpha I$ and $(1-\alpha)I$ respectively. Other electrodes which are not being used to input or output current on the same horizontal plane 100 or electrodes in different horizontal planes are serving as sensors to measure the electrical voltage signals passing through the object 2, which is to be imaged. Since the target 3 is located within the range of electrode array 11, the electrical voltage signals correspond to the target 3 will be measured and detected. If $\alpha$ is equal to 0, it means that only an alternating current I is outputted to a horizontal driving electrode 1111 (the $2^{nd}$ horizontal driving electrode 1111 has zero alternating current), which is identical to standard 3D EIT method; if a is equal to 0.5, it then means that alternating currents I/2 are being outputted to each of the two horizontal driving electrodes 1111. No matter what $\alpha$ is, the net alternating current input is I and net alternating current output is also I.

Therefore, the plurality of electrodes 11001 of the electrode array 11 may be divided into multiple horizontal planes 100. The electrodes 11001 in each horizontal plane 100 are sequentially selected to be driving electrodes to input/output the alternating current while the other electrodes which are not selected (either on the same plane or on the different plane) are served as sensors to measure the electrical voltage signals.

In FIG. 3B, the plurality of electrodes 11001 located at the same vertical plane 101 in the electrode array 11 are defined as a vertical electrode set 112 and then a plurality of electrodes 11001 are selected from the vertical electrode set 112 to be vertical driving electrodes 1121. Next, a small amount of alternating current I is inputted from one of the plurality of vertical driving electrodes 1121, and the other two vertical driving electrodes 1121 output the alternating current $\alpha I$ and $(1-\alpha)I$ respectively. Other electrodes which are not being used to output or input current on the same vertical plane or the different plane are served as sensors to measure the electrical voltage signals passing through the object 2, which is to be imaged. Since the target 3 is located within the range of electrode array 11, the electrical voltage signals correspond to the target 3 will be measured and detected.

Therefore, the plurality of electrodes 11001 of the electrode array 11 may be divided into multiple vertical planes 101. The electrodes 11001 in each vertical plane 101 are sequentially selected to be driving electrodes to input/output the alternating current while the other electrodes which are not selected (either on the same vertical plane or on the different vertical plane) are served as sensors to measure the electrical voltage signals.

In FIG. 3C, the plurality of electrodes 11001 of the electrode array 11 are divided into multiple horizontal planes 100 and multiple vertical planes 101. As shown in the figure, the plurality of driving electrodes are then sequentially selected according to the manner described above to input/output the alternating current while the other electrodes which are not selected (either on the same plane or on the different plane) are served as sensors to measure the electrical voltage signals. A small amount of alternating current I is inputted to one of the plurality of horizontal driving electrodes 1111 and the other two horizontal driving electrodes 1111 output the alternating current $\alpha I$ and $(1-\alpha)I$ respectively. Meanwhile, a small amount of alternating current I is inputted to one of the plurality of vertical driving electrodes 1121 and the other two vertical driving electrodes 1121 output the alternating current $\beta I$ and $(1-\beta)I$ respectively. i.e., $\alpha$ and $\beta$ may be different values and may be respectively and independently adjusted depending on requirements.

It should be noted that the horizontal plane and/or the vertical plane served as the plane described above is for example only and should not be limited thereto. The plane may also be an inclined plane with arbitrary angle.

Figure 3D:
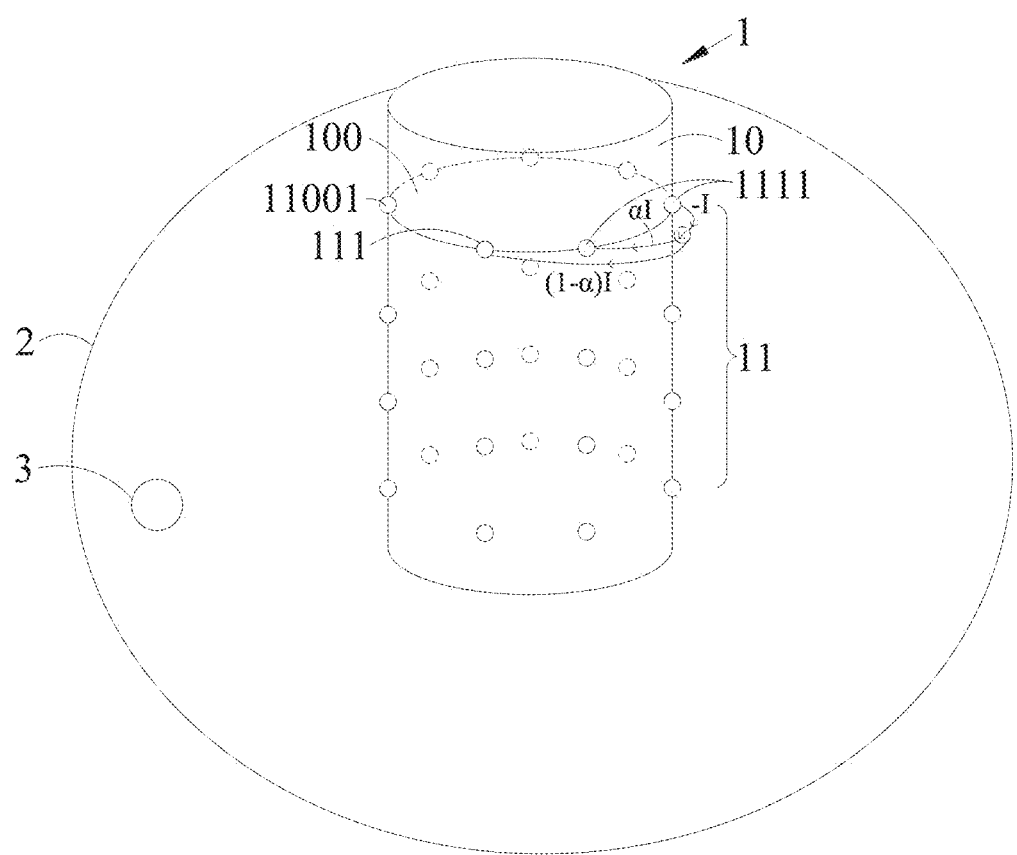
FIG. 3D is another schematic diagram of the horizontal plane according to the third embodiment of the three dimensional electrical impedance tomographic method of the present invention.
Figure 3E:
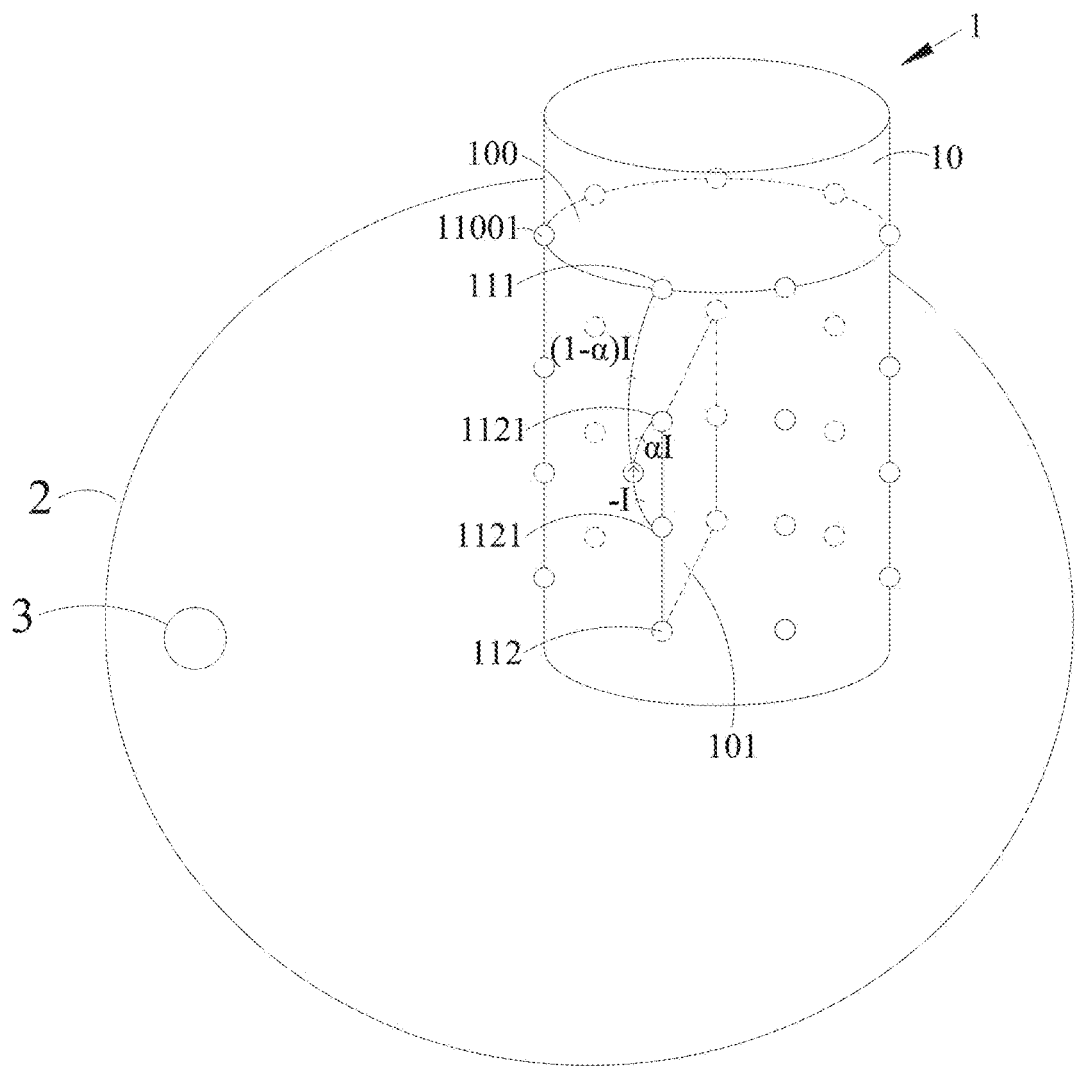
FIG. 3E is another schematic diagram of the vertical plane according to the third embodiment of the three dimensional electrical impedance tomographic method of the present invention.
Figure 3F:
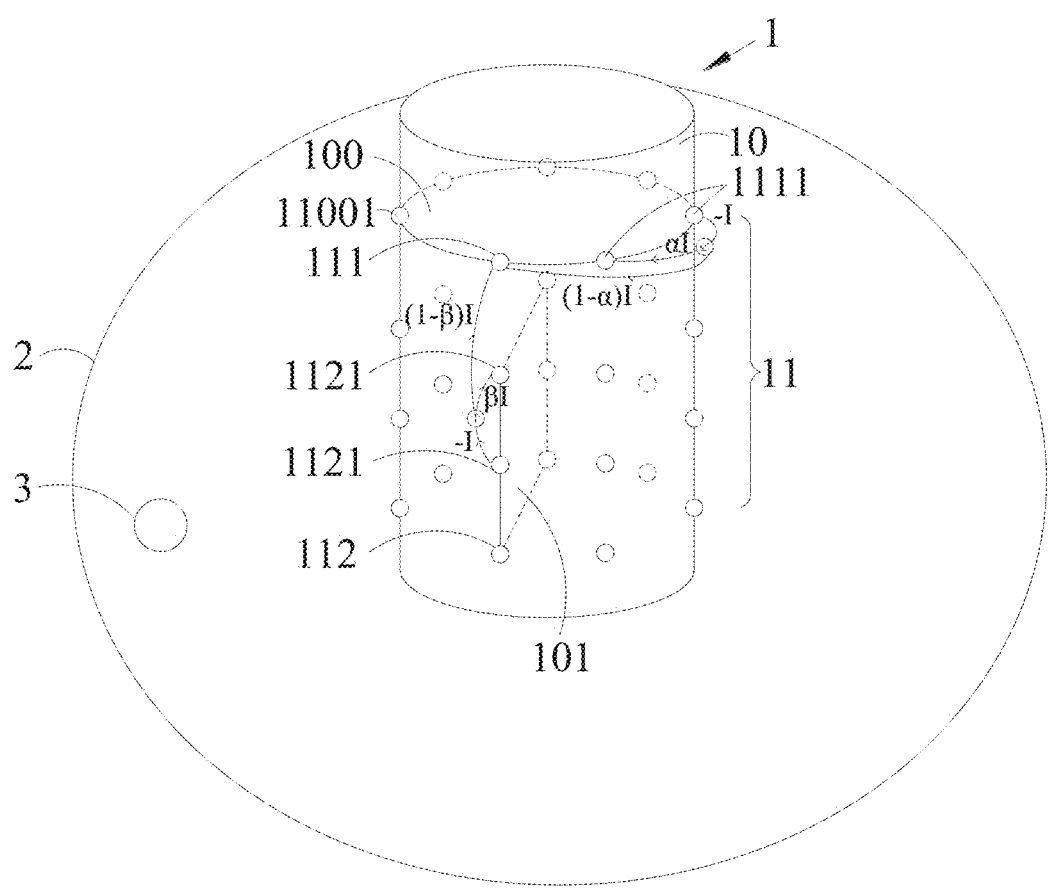
FIG. 3F is another schematic diagram of using the horizontal and vertical plane at the same time according to the third embodiment of the three dimensional electrical impedance tomographic method of the present invention.

Please refer to FIG. 3D, FIG. 3E and FIG. 3F, which are another schematic diagram of the horizontal plane, another schematic diagram of the vertical plane and another schematic diagram of using the horizontal and vertical plane at the same time respectively according to the third embodiment of the three dimensional electrical impedance tomographic method of the present invention. In the figures, the clustering method and the driving method of the electrodes are similar to the above descriptions and the difference is that FIG. 3D, FIG. 3E and FIG. 3F take outward-looking as an example for illustration. The implantation body 1 has a cylindrical bearing surface 10. An electrode array 11 consists of a plurality of electrodes 11001 is mounted on the bearing surface 10. The probe-shape implantation body 1 is implanted in the object 2, which is to be imaged and a target 3 is formed within the object 2. The electrical impedance signals corresponding to target 3 may be obtained through the driving and measurement methods described above.

Figure 4:
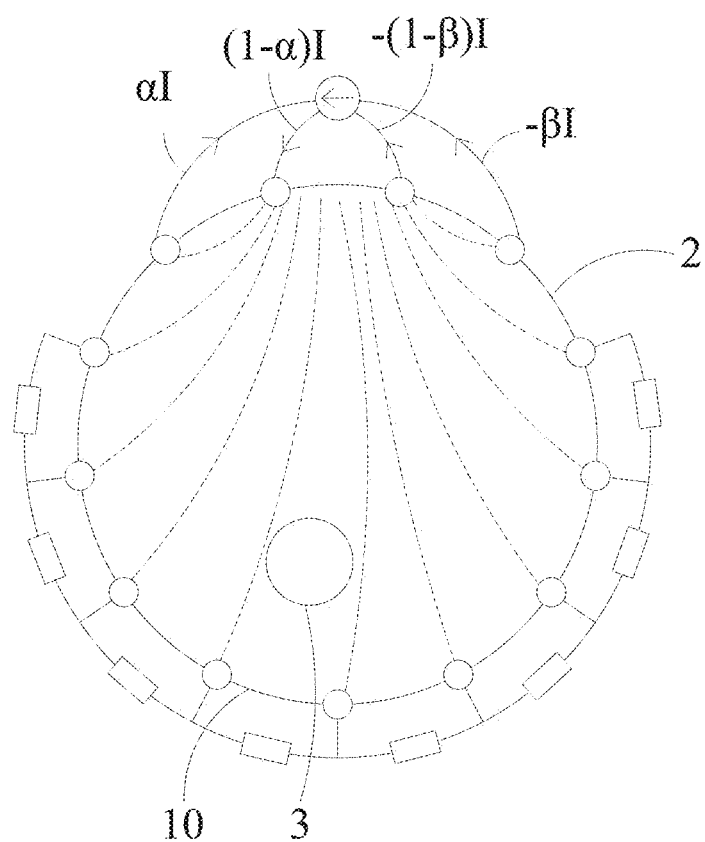
FIG. 4 is a top view schematic diagram of the electrical impedance tomography utilizing the current control technology according to the three dimensional electrical impedance tomographic method of the present invention.
Figure 5:
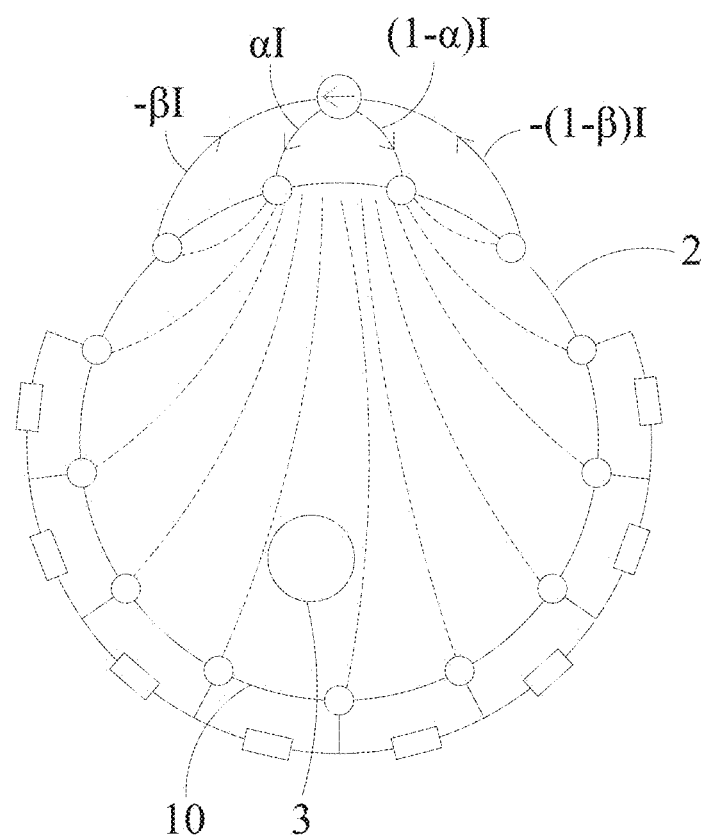
FIG. 5 is a top view schematic diagram of another electrical impedance tomography utilizing the current control technology according to the three dimensional electrical impedance tomographic method of the present invention.

Please refer to FIG. 4 and FIG. 5 together, which are top view schematic diagrams of the electrical impedance tomography utilizing the current control technology according to the three dimensional electrical impedance tomographic method of the present invention. FIG. 4 and FIG. 5 are illustrated by the application of the electrical impedance tomography of two dimensional planes, but it should not be limited thereto.

The difference between the embodiment shown by FIG. 4 and FIG. 5 and the embodiments described above is that the present embodiment has selected four driven electrodes in advance to input/output current respectively.

FIG. 4 shows that the current control technology is applied to the electrical impedance tomography in order to further increase the resolution of tomographic images. In FIG. 4, the electrode controller receives a control signal and then drives the four driven electrodes which are selected in advance according to the control signals, but this is for example only and should not be limited thereto. The driving alternating currents applied to these four electrodes respectively are $-\beta I$, $-(1-\beta)I$, $\alpha I$ and $(1-\alpha)I$, wherein a positive sign represents that the direction of current is toward the input electrodes, a negative sign represents that the direction of current is from the output electrodes, and $\alpha$ and $\beta$ represent the power control parameters transmitted by the control signal and may be set respectively and independently. FIG. 5 shows different current configurations which are also within the scope of the present invention.

Meanwhile, other electrodes which are not driven on the same plane are serving as sensors to measure the electrical voltage signals passing through the object 2, which is to be imaged. After the electric voltage signals are transmitted to a data acquisition device 14 (as described in FIG. 1), a set of voltage data is formed in association with geographical location data of the driven electrodes and the receiving electrodes on the plane. Multiple sets of voltage data may be obtained by applying any one of the two methods described above on the different plane repeatedly and the multiple sets of voltage data are sent to the computing device 15. A three dimensional electrical impedance tomographic image corresponding to the object to be imaged is then formed by combining the plurality of sets of voltage data and the corresponding control signals through a 3D reconstruction algorithm.

Figure 6A:
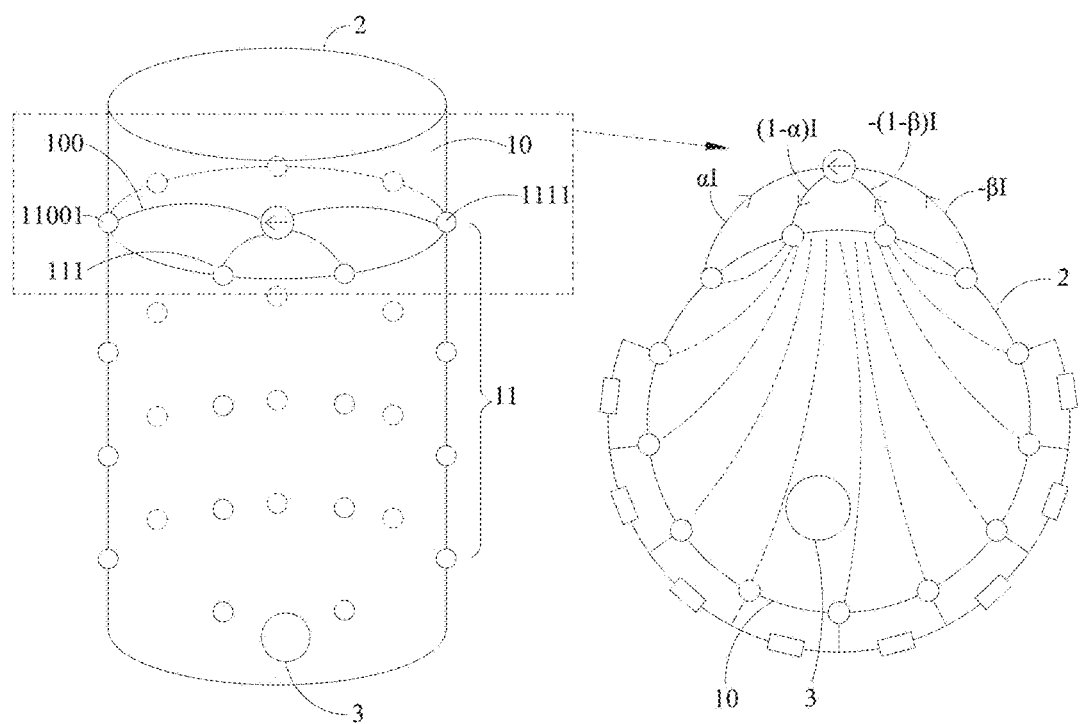
FIG. 6A is a schematic diagram of electrical impedance tomography utilizing the current control technology on the horizontal plane according to the three dimensional electrical impedance tomographic method of the present invention.
Figure 6B:
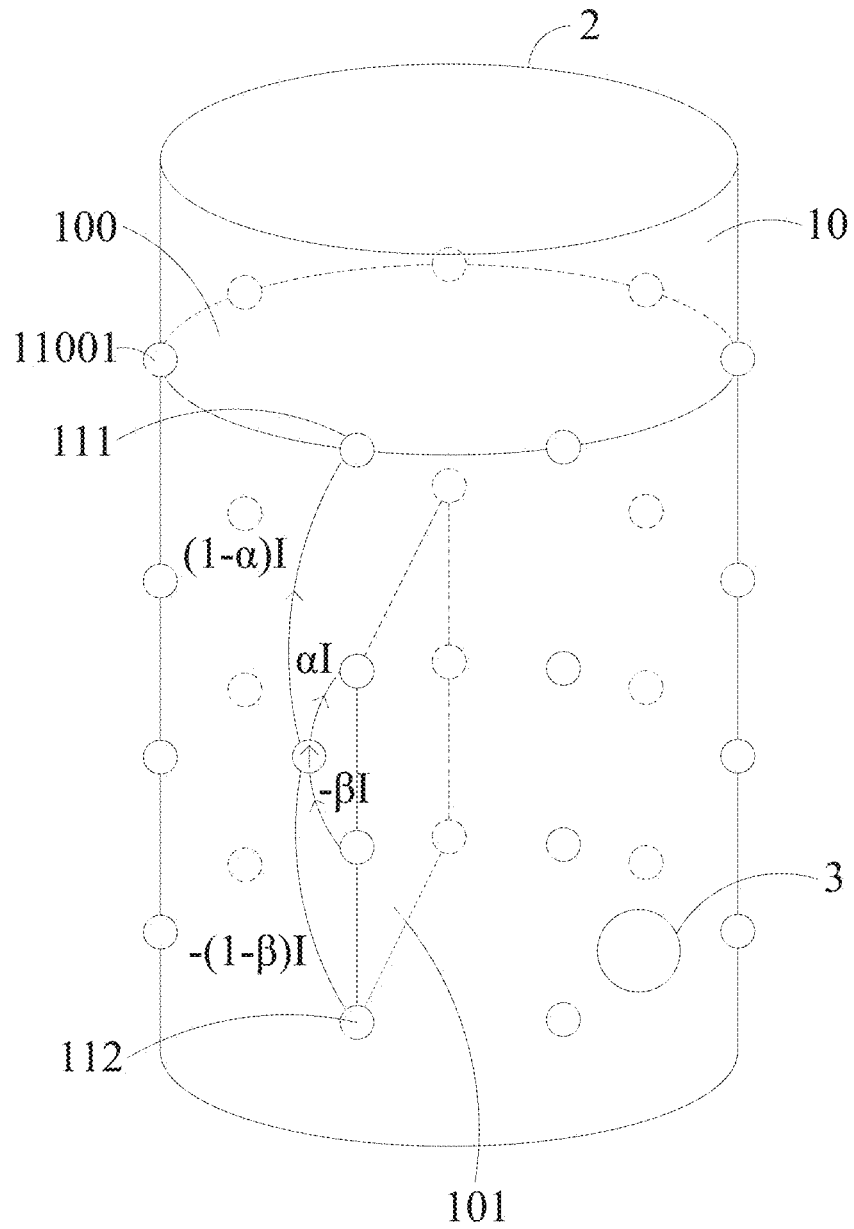
FIG. 6B is a schematic diagram of electrical impedance tomography utilizing the current control technology on the vertical plane according to the three dimensional electrical impedance tomographic method of the present invention.
Figure 6C:
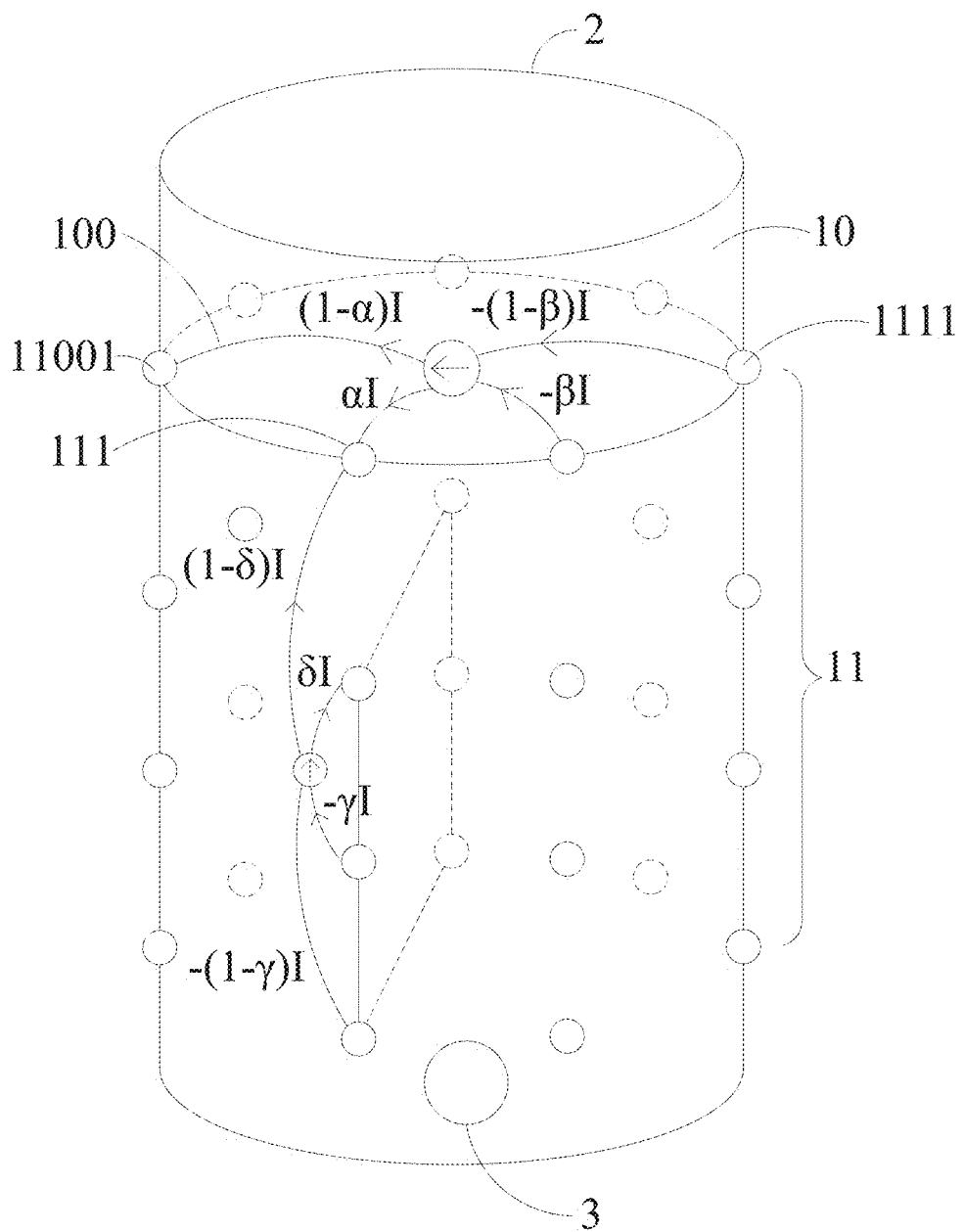
FIG. 6C is a schematic diagram of electrical impedance tomography utilizing the current control technology on the horizontal and the vertical plane according to the three dimensional electrical impedance tomographic method of the present invention.

Please refer to FIG. 6A to FIG. 6C, which shows that the current control technology (similar to the current control in FIG. 4 and FIG. 5) may be utilized to the electrical impedance tomography of the horizontal plane, the electrical impedance tomography of the vertical plane and the electrical impedance tomography of both of the horizontal and the vertical planes. In the present embodiment, inward-looking is taken as an example. However, it may also be applied to outward-looking. Moreover, α and β may be different values and may be respectively and independently adjusted depending on requirements.

Please refer to FIG. 7, which is a flowchart according to the third embodiment of the three dimensional electrical impedance tomographic method of the present invention. According to an objective of the present invention, a three dimensional electrical impedance tomographic method is provided, which includes the following steps:

in step S1, an implantation body is disposed in an object to be imaged and the implantation body has a bearing surface. For implementation, the shape of the bearing surface may be spherical, cylindrical or irregular shaped object like a head or abdomen of a human body;

in step S2, an electrode array is disposed on the bearing surface. The electrode array has a plurality of electrodes;

in step S3, an electrode controller is disposed. The electrode controller is electrically connected to the plurality of electrodes respectively;

in step S4, the plurality of electrodes located at the same horizontal plane on the electrode array are defined as a horizontal electrode set. The electrode array may include a plurality of horizontal electrode sets;

in step S5, a plurality of horizontal control signals are generated. The plurality of horizontal control signals include a horizontal selection parameter respectively;

in step S6, one of the plurality of horizontal control signals is received through the electrode controller. Any horizontal electrode set is selected by the electrode controller according to the horizontal selection parameter of the horizontal control signal and then a plurality of horizontal driving electrodes are selected from the selected horizontal electrode set;

in step S7, when the electrode controller drives the plurality of horizontal driving electrodes, all other electrodes except the plurality of horizontal driving electrodes in the selected horizontal electrode sets are used to receive signals transmitted by the plurality of horizontal driving electrodes in order to form a set of horizontal voltage data;

Next, this method is performed in connection with the vertical plane according to the operation similar to that of the horizontal plane described above.

in step S8, the plurality of electrodes located at the same vertical plane on the electrode array are defined as a vertical electrode set. The electrode array may include a plurality of vertical electrode sets;

in step S9, a plurality of vertical control signals are generated. The plurality of vertical control signals include a vertical selection parameter respectively;

in step S10, one of the plurality of vertical control signals is received through the electrode controller. Any vertical electrode set is selected by the electrode controller according to the vertical selection parameter of the vertical control signal and then a plurality of vertical driving electrodes are selected from the selected vertical electrode set;

in step S11, when the electrode controller drives the plurality of vertical driving electrodes, all other electrodes except the plurality of vertical driving electrodes in the selected vertical electrode sets are used to receive signals transmitted by the plurality of vertical driving electrodes in order to form a set of vertical voltage data;

in step S12, a solver, such as a linear solver or nonlinear solver is performed to combine the plurality of horizontal control signals, the plurality of sets of horizontal voltage data, the plurality of vertical control signals and the plurality of sets of vertical voltage data in order to form the three dimensional electrical impedance tomographic images.

For implementation, the plurality of horizontal control signals further include a horizontal power control parameter respectively. The electrode controller respectively controls a power output ratio of any electrode in the plurality of horizontal driving electrodes by the horizontal power control parameter and a first distribution condition. The plurality of vertical control signals further include a vertical power control parameter respectively. The electrode controller respectively controls a power output ratio of any electrode in the plurality of vertical driving electrodes by the vertical power control parameter and a second distribution condition.

For implementation, the first distribution condition is that a current distribution is performed according to the horizontal power control parameter, and a sum of current of the plurality of horizontal driving electrodes is made to be zero. The second distribution condition is that the current distribution is performed according to the vertical power control parameter, and a sum of current of the plurality of vertical driving electrodes is made to be zero.

Please refer to FIG. 8, which is a flowchart according to the fourth embodiment of the three dimensional electrical impedance tomographic method of the present invention. According to another objective of the present invention, a three dimensional electrical impedance tomographic method is again provided, which includes the following steps:

in step S21, an implantation body is disposed in an object to be imaged and the implantation body has a bearing surface. The shape of the bearing surface may be spherical, cylindrical, or irregular shaped object like a head or abdomen of a human body;

in step S22, an electrode array is disposed on the bearing surface. The electrode array has a plurality of electrodes;

in step S23, an electrode controller is disposed. The electrode controller is electrically connected to the plurality of electrodes respectively;

in step S24, the plurality of electrodes located at the same plane on the electrode array are defined as a plane electrode set. The electrode array may include a plurality of plane electrode sets. For implementation, the plane may be a horizontal plane, a vertical plane or an inclined plane with angle;

in step S25, a plurality of plane control signals are generated. The plurality of plane control signals include a plane selection parameter and a plane power control parameter respectively;

in step S26, the plurality of plane control signals are received through the electrode controller respectively. Any plane electrode set is selected by the electrode controller according to the plane selection parameter of the plane control signal and then a plurality of plane driving electrodes are selected from the selected plane electrode set;

in step S27, power output ratios of any electrode in the plurality of plane driving electrodes are respectively controlled by the plane power control parameter and a first distribution condition;

in step S28, when the electrode controller drives the plurality of plane driving electrodes, all other electrodes except the plurality of plane driving electrodes in the selected plane electrode sets are used to receive signals transmitted by the plurality of plane driving electrodes in order to form a set of plane voltage data;

in step S29, a calculation is performed to combine the plurality of plane control signals and the plurality of sets of plane voltage data in order to form a three dimensional electrical impedance tomographic image corresponding to the object to be imaged.

For implementation, the plurality of plane control signals may be current signals. The first distribution condition is that a current distribution is performed according to the plane power control parameter, and a sum of current of the plurality of plane driving electrodes is made to be zero.

In conclusion, the three dimensional electrical impedance tomographic method of the present invention executes the injection of current into the object to be imaged and measure differential voltage of all the electrodes not being used to input or output current, then by adjusting the control signal, e.g. α in FIG. 3, it is possible to increase the number of independently measured data when compare with standard 3D EIT method. The measured data is then used to reconstruct a three dimensional image, but due to the significantly more number of measurements a better three dimensional image reconstruction is possible. Please refer to FIG. 9A, FIG. 9B, and FIG. 9C, which depicts a comparison diagram which compares the image according to the three dimensional electrical impedance tomographic method of the present invention with the image of the conventional electrical impedance tomography technique.

Figure 9A:
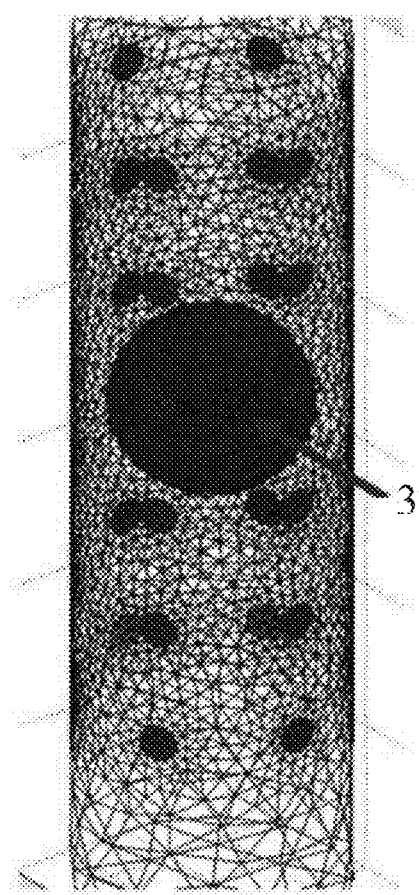
FIG. 9A, FIG. 9B, and FIG. 9C is a comparison diagram which compares the image according to the three dimensional electrical impedance tomographic method of the present invention with the image of the conventional electrical impedance tomography technique.
Figure 9B:
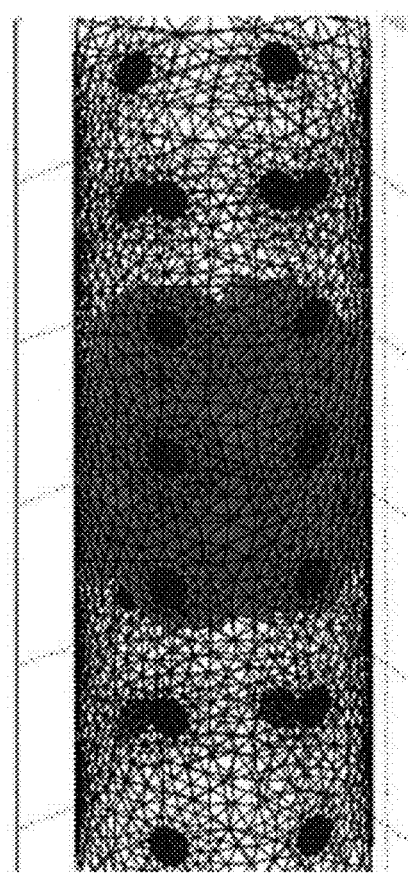
Figure 9C:
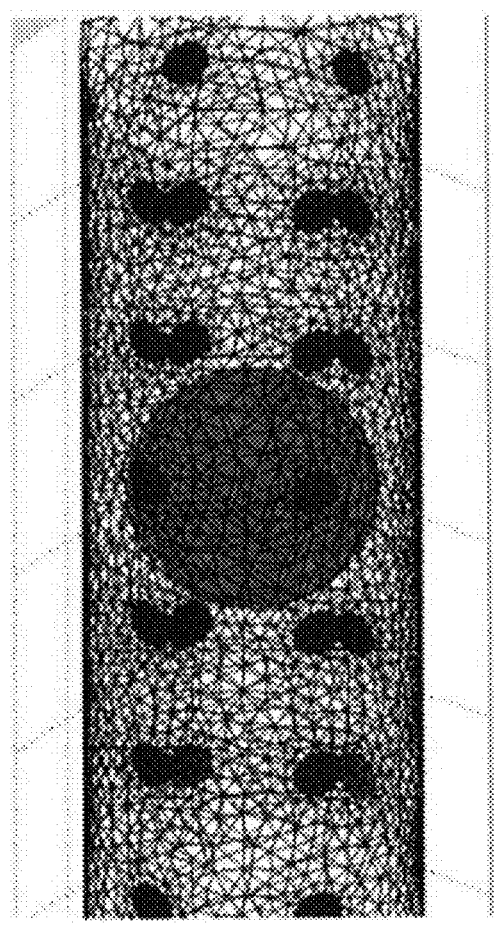
Figure 10A:
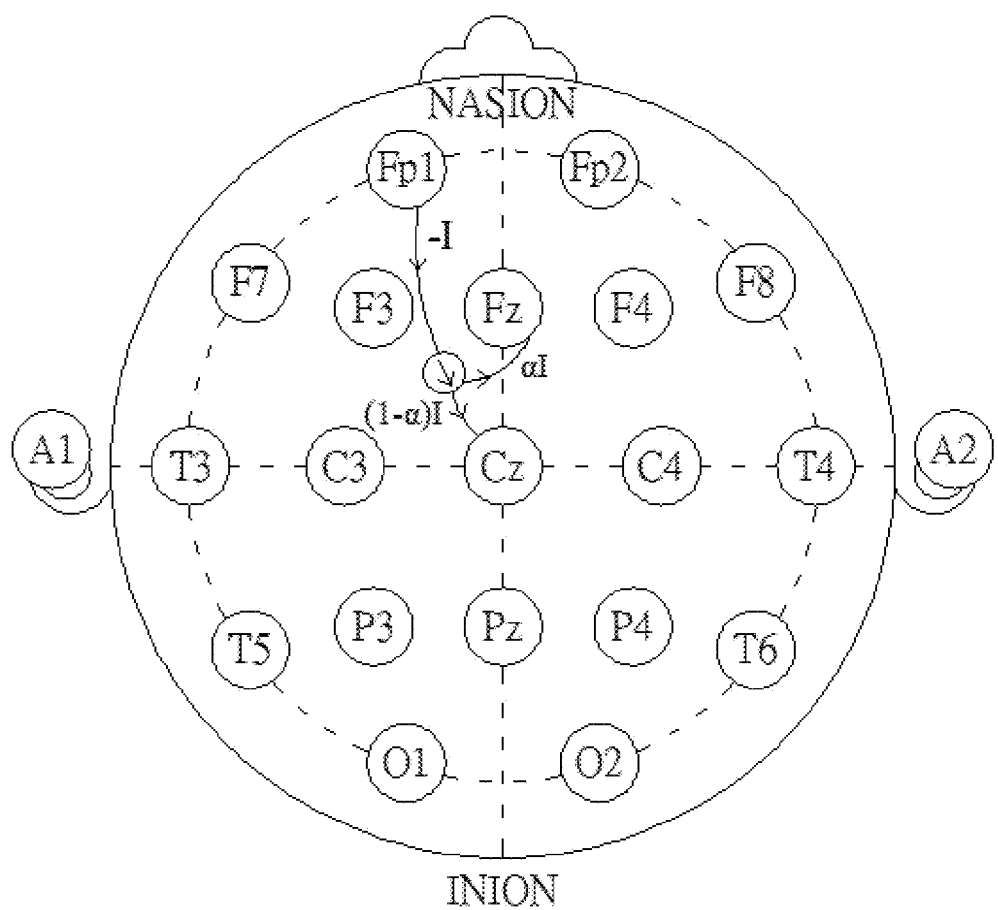
FIG. 10A, FIG. 10B, FIG. 11A and FIG. 11B are schematic diagrams of another application according to the three dimensional electrical impedance tomographic method of the present invention.
Figure 10B:
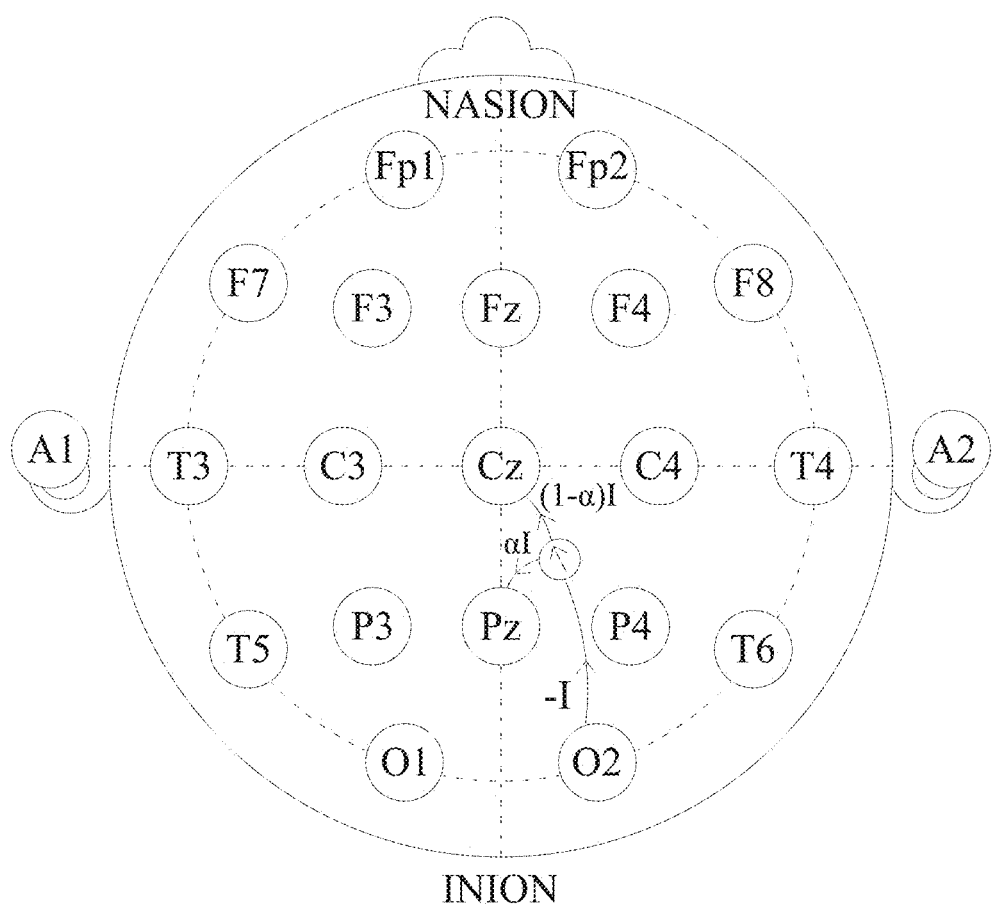

In FIG. 9A, FIG. 9B, and FIG. 9C, FIG. 9A represents a target to be pictured. FIG. 9B is a three dimensional image generated by using the conventional electrical impedance tomography. FIG. 9C is a three dimensional image generated by using the three dimensional electrical impedance tomographic method of the present invention. It can be obviously seen from the figure that the three dimensional electrical impedance tomographic method of the present invention can generate images which more look like the target and more precise and complete three dimensional information may be reconstructed using the present invention.

Please refer to FIG. 10A, FIG. 10B, FIG. 11A and FIG. 11B, which are schematic diagrams of the three dimensional electrical impedance tomographic method of the present invention applied to a head of human body. As shown in the figure, the electrodes in the electrode array may be configured in accordance with a contour of the head. In the figures, they are made into circular arc shapes and the detection may still be performed according to the detection method described above to form the three dimensional electrical impedance tomographic images of the head. In this way, the disposition position and method of the electrodes in the electrode array of the present invention may be adjusted in accordance with the detection target without the limitations of the above examples.

Figure 12:
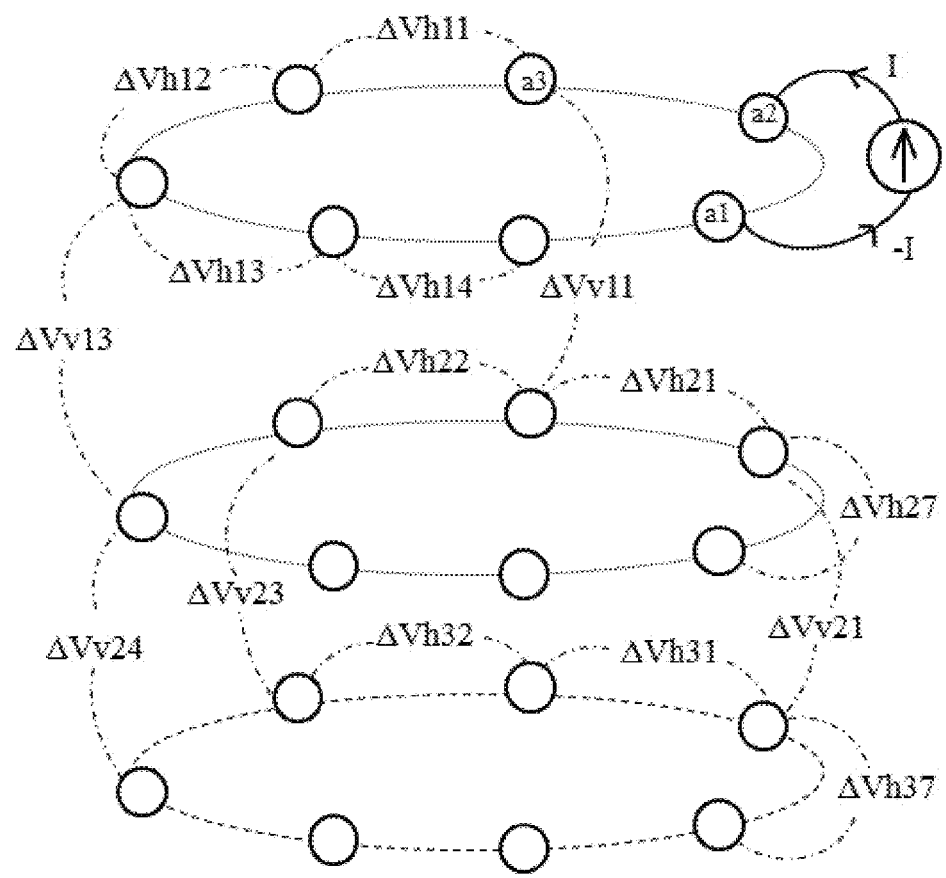
FIG. 12 is a first schematic diagram of implementing the current control technology according to the three dimensional electrical impedance tomographic method of the present invention.

Please refer to FIG. 12, which is a schematic diagram according to the fifth embodiment of the three dimensional electrical impedance tomographic method of the present invention. In the fifth embodiment, the detailed illustration on how to obtain a three dimensional electrical impedance tomographic images through the current control technology is given. In FIG. 12, for the convenience of illustration, 21 electrodes in the electrode array are divided into three groups, which are vertically and horizontally separated according to the figure. Each group of electrodes is arranged in a circular ring shape. When the current control is performed, a current source is first provided and at least two electrodes are selected to input and output a current I. As shown at the upper right corner in FIG. 12, two electrodes at the rightmost and the topmost group a1 and a2 are selected to input and output the current I, wherein the current I is outputted from the electrode a1 and inputted to the electrode a2. It should be noted that the number of the electrodes which are selected to input and output current may be larger than two. The description is similar to that described by the previous content and is not repeated herein.

After the current I is inputted or outputted through the selected electrodes, voltage values can be measured from each of the two adjacent electrodes in addition to the selected electrodes. As shown in FIG. 12, four voltage values $\Delta Vh11$, $\Delta Vh12$, $\Delta Vh13$ and $\Delta Vh14$ can be measured in total from the topmost group of electrodes. Similarly, seven voltage values $\Delta Vh21 \sim \Delta Vh27$ can be measured in total from the middle group of seven electrodes and seven voltage values $\Delta Vh31 \sim \Delta Vh37$ can be measured in total from the bottommost group of seven electrodes.

Next, the voltage values can also be measured in the vertical direction. For example, five voltage values $\Delta Vv11 \sim \Delta Vv15$ (the voltage values not measured from the selected two electrodes) can be measured in total by matching upper pair of electrodes and lower pair of electrodes between the topmost group of seven electrodes and the middle group of seven electrodes. Similarly, seven voltage values $\Delta Vv21 \sim \Delta Vv27$ can be measured in total between the middle group of seven electrodes and the bottommost group of seven electrodes.

Therefore, in FIG. 12, two electrodes are selected each time to input and output current and 30 voltage values (30=4+7+7+5+7) can be measured in total.

Then, the two selected electrodes are changed. For example, two electrodes a2 and a3 are selected to input and output the current I in the counterclockwise direction. As described above, 30 voltage values are also again measured. Thus, 210 voltage values (210=7*30) can be measured in total by selecting the electrodes in turn from the topmost group of electrodes and measuring voltage values. The same process is kept performing in the middle group of electrodes and the bottommost group of electrodes and 420 voltage values are measured.

Therefore, in the case of dividing 21 electrodes into three groups which are vertically and horizontally separated as shown in FIG. 12, 630 voltage values can be measured. These 630 voltage values can be used to reconstruct a three dimensional electrical impedance tomographic image. Next, arbitrary plurality of electrodes on the same plane are selected and controlled by using the current control technology. Theses 21 electrodes can be used to increase the number of measured voltage values to many times more than 630 by using the current control scheme as proposed in the present invention. As the number of measured voltage increases, the resolution of the three dimensional electrical impedance tomographic image can be increased and the precision of image can be enhanced at the same time.

Figure 11A:
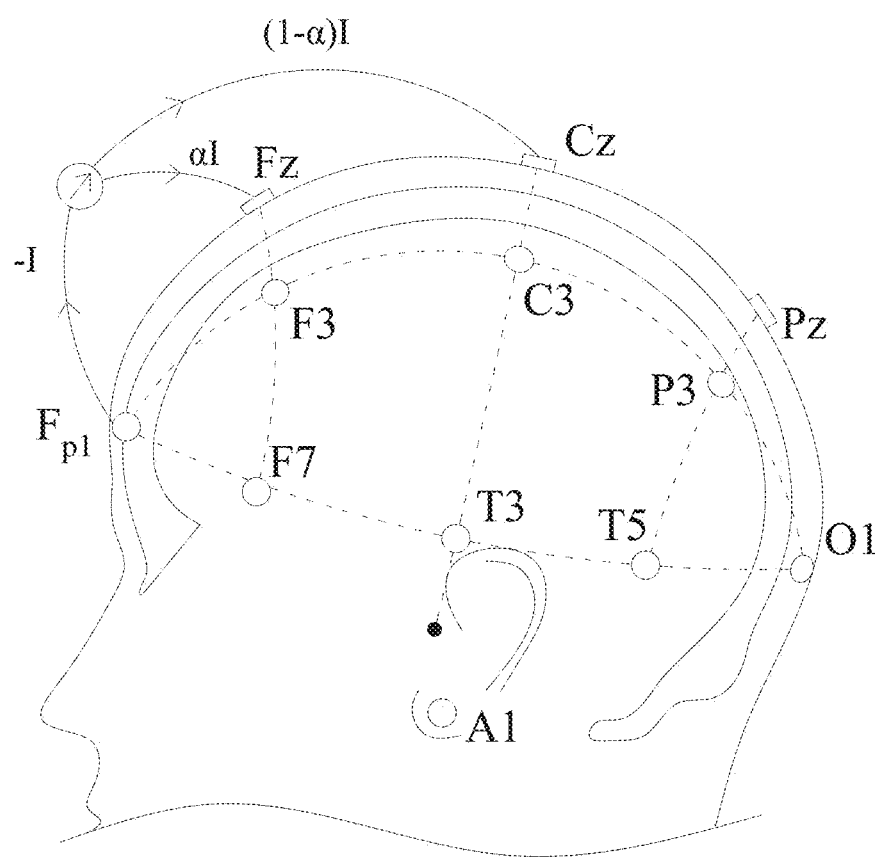
Figure 11B:
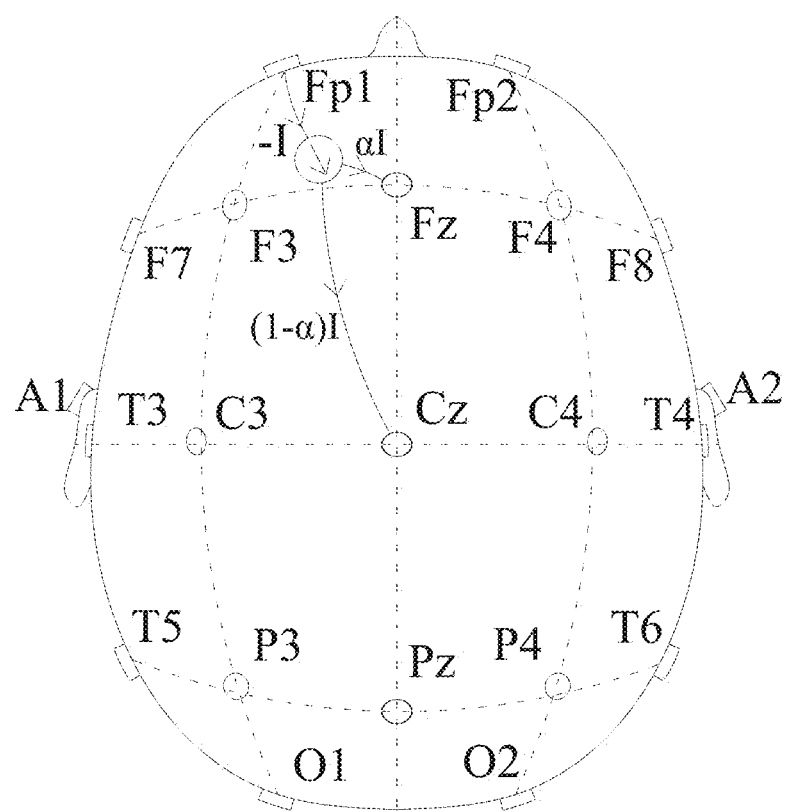

It should be noted that dividing the electrodes into multiple groups which are vertically and separately arranged respectively in FIG. 12 is merely for convenience of illustration. Also, the electrodes in each group are arranged on the same plane vertically. However, the present invention is not thus limited. In the other embodiments of the present invention, a plurality of electrodes may be configured on a curve surface in a non-coplanar way as shown in FIG. 11A and FIG. 11B. The illustration on how the electrodes configured in the non-coplanar way implementing the current control technology is further given as follows.

Please refer to FIG. 13A to FIG. 13K, which are second schematic diagrams of implementing the current control technology according to the three dimensional electrical impedance tomographic method of the present invention. It should be noted that the electrodes are depicted as an arrangement of array in FIG. 13A to FIG. 13K is merely for convenience of illustration. However, the present invention is not limited thereto. Any current control technology implemented in FIG. 13A to FIG. 13K may also be applicable to the electrode arrangement in FIG. 10A and FIG. 10B.

Figure 13A:
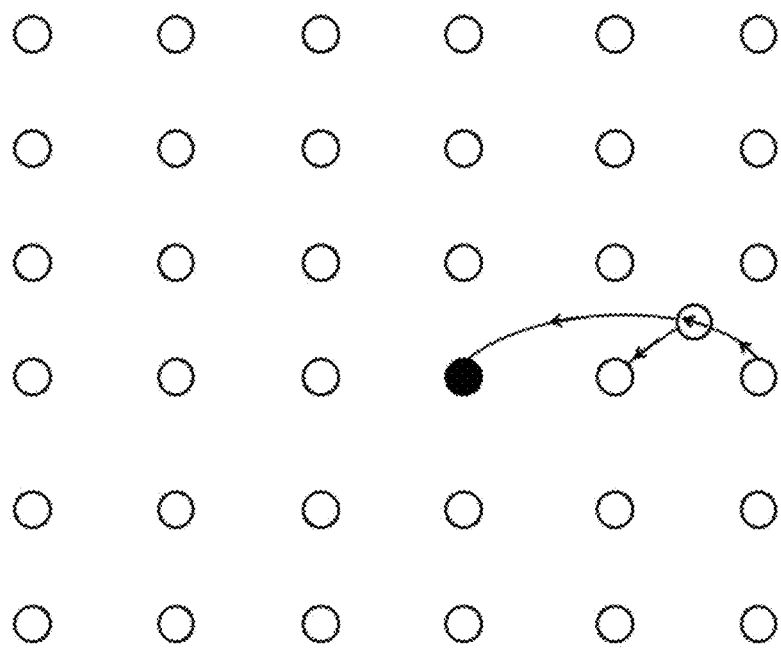
FIG. 13A to FIG. 13K are second schematic diagrams of implementing the current control technology according to the three dimensional electrical impedance tomographic method of the present invention.
Figure 13B:
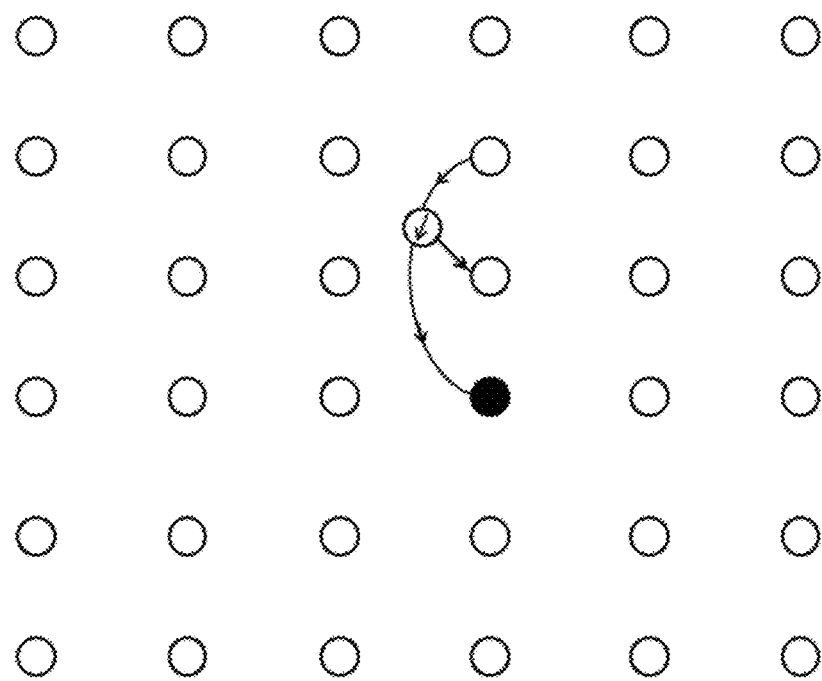
Figure 13C:
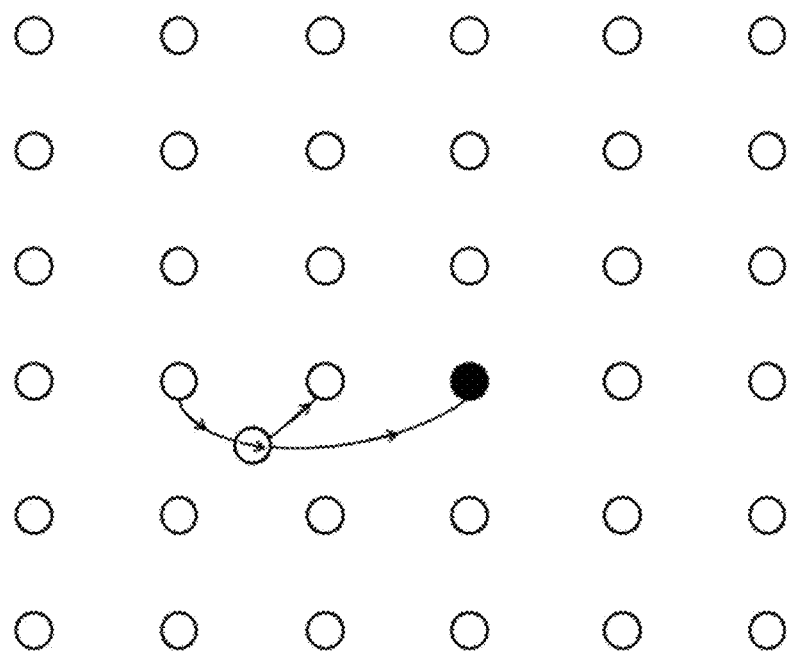
Figure 13D:
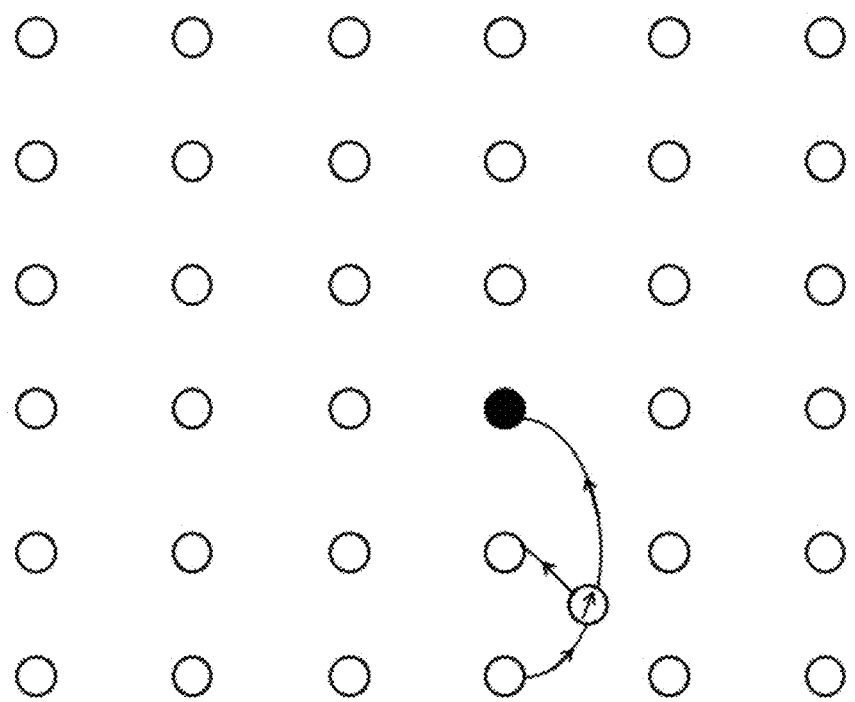
Figure 13E:
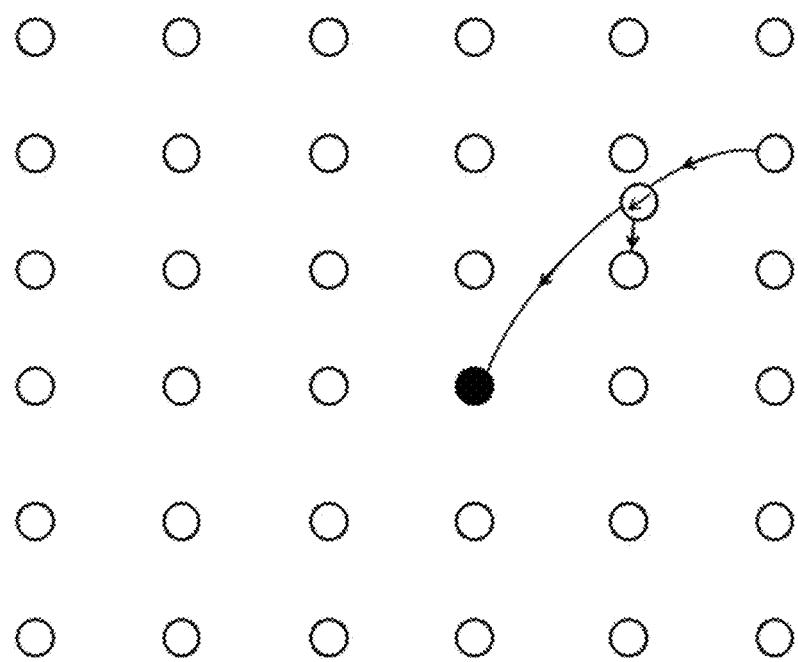
Figure 13F:
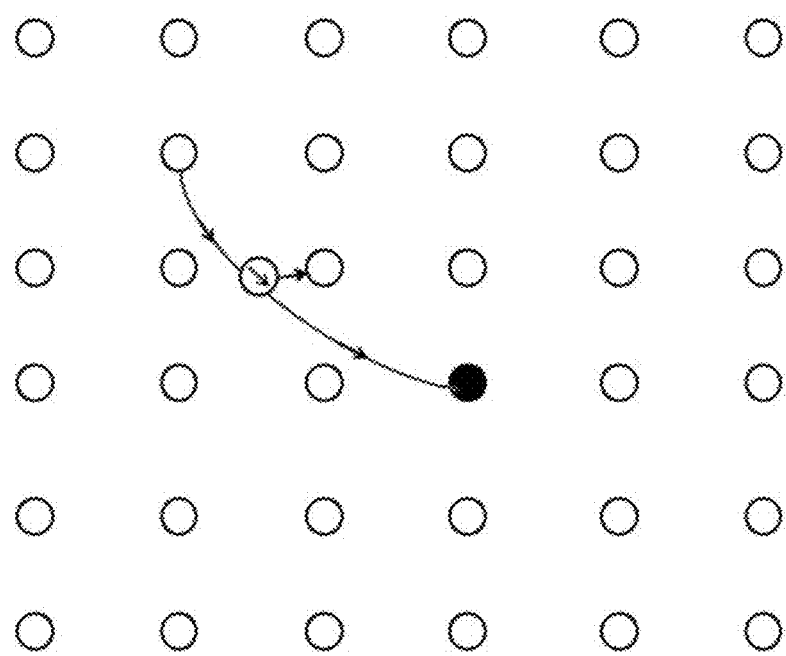
Figure 13G:
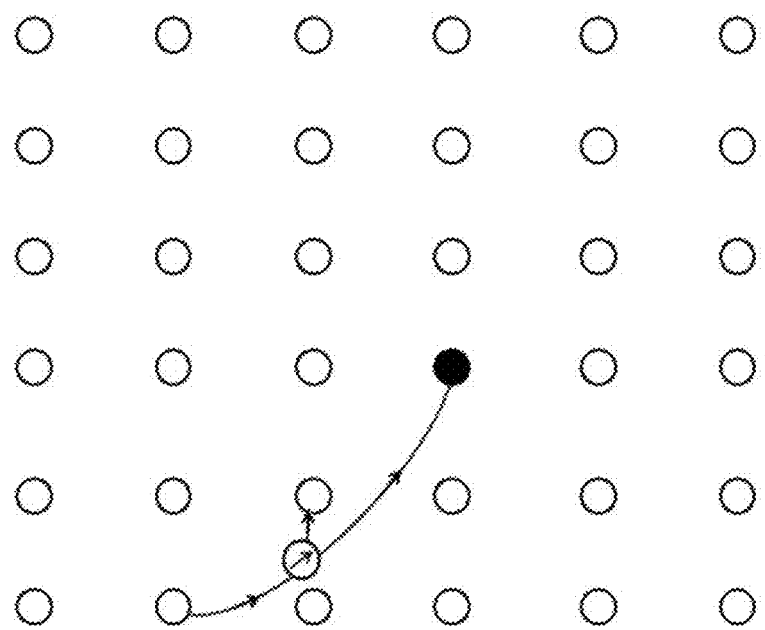
Figure 13H:
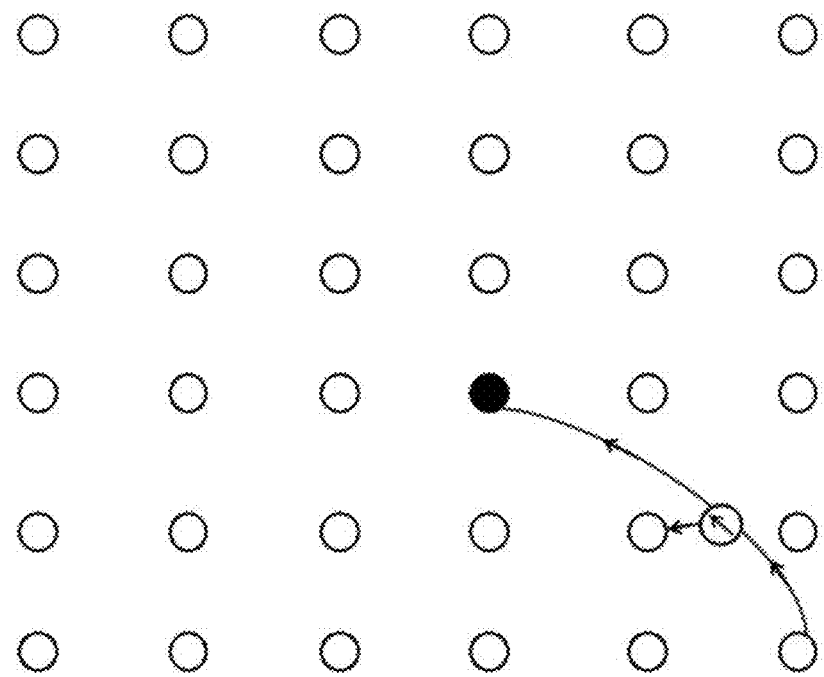

Please refer to FIG. 13A, when the current control technology is implemented, an electrode which is shown as a black dot in the figure is first selected. Next, at least one electrode is sequentially selected among the electrodes around the selected electrodes to implement the current control. FIG. 13A to FIG. 13K are illustrated through implementing the current control by three electrodes, but are not limited thereto. The current control using such as three electrodes (like FIG. 3 and FIG. 11) or four electrodes (like FIG. 4 to FIG. 6) previously described may also be applicable.

Please refer to FIG. 13A to FIG. 13D, which depict the current control implemented by using three electrodes with different positions (e.g. right, top, left, bottom) selected sequentially in a counterclockwise direction after an electrode (the black electrode) is selected as a center. Another selection method (such as the position of another two electrodes are upper right, upper left, bottom left, bottom right) are also shown in FIG. 13E to FIG. 13H. When the current is inputted and outputted each time, the voltage values between of any two electrodes among the other electrodes are measured. Wherein the method of operation is as same as that illustrated in FIG. 12 and is not repeated herein.

Figure 13I:
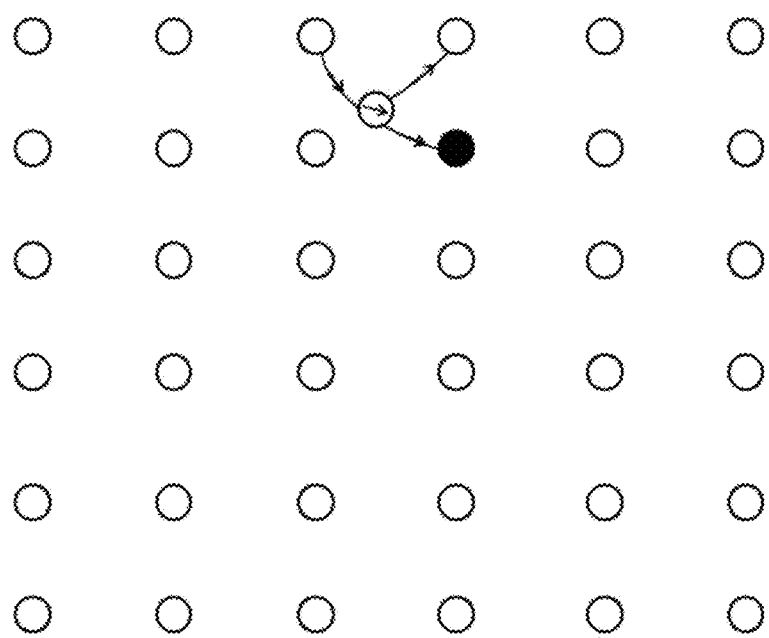

Then, the electrode which is served as the center is changed. As shown in FIG. 13I, the electrode which is served as the center is moved upwardly. When it is close to the edge, another way of another two electrodes is selected.

Figure 13J:
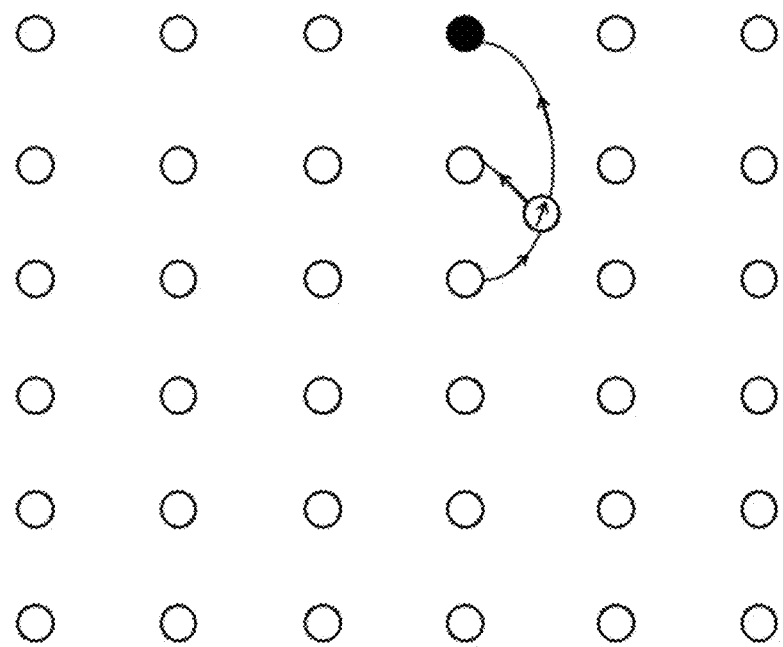
Figure 13K:
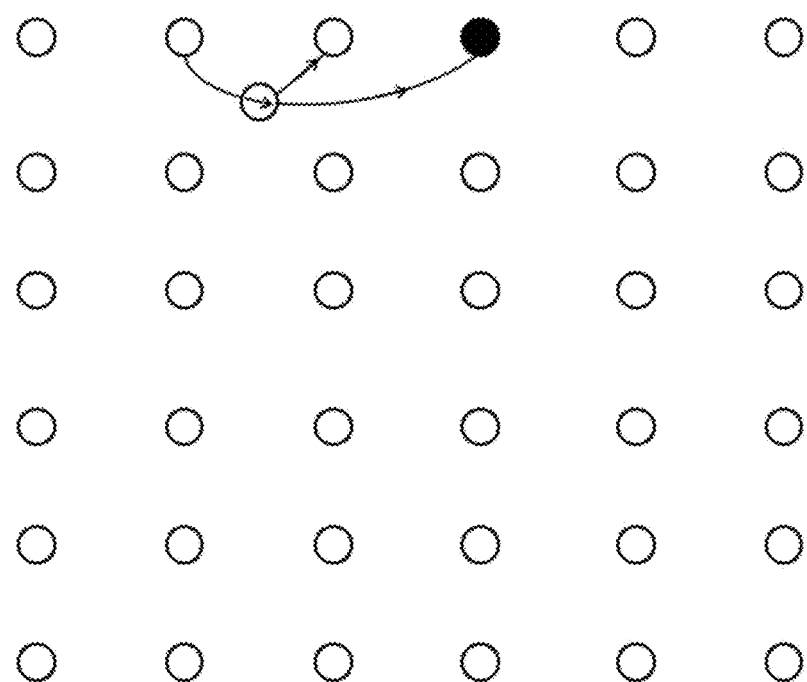

Next, as shown in FIGS. 13J and 13K, when the electrode which is served as the center is moved to the upper edge, the left side, the right side and the lower side electrodes can still be selected to implement the current control technology. The positions of each selected electrode above are exemplary only and the present invention is not limited thereto.

Therefore, as known from FIG. 13A to FIG. 13H, it is not necessary to arrange in array, or in a significant co-planar way, or significant grouping in the vertical direction for the electrodes of the present invention which can also implement the current control in order to measure a large amount of voltage values and thereby form the three dimensional electrical impedance tomographic images.

Although the present invention has been particularly displayed and described with reference to the exemplary embodiments thereof, it will be understood by any skills in the relevant technical fields that various changes can be made to the implementation of the present invention in forms and in details without departing from the spirit and scope of the present invention defined by the appended claims below and its equivalence.

What is claimed is:

1. A three dimensional electrical impedance tomographic method, used to form a three dimensional electrical impedance tomographic image corresponding to an object to be imaged, the three dimensional electrical impedance tomographic method comprising the following steps:
   providing an electrode array, the electrode array having a plurality of electrodes, wherein the electrode array is located at an inner section or an outer section of the object to be imaged;
   disposing an electrode controller, the electrode controller electrically connected to the plurality of electrodes respectively;
   defining the plurality of electrodes located at the same plane on the electrode array as a plane electrode set, and the electrode array comprising a plurality of plane electrode sets;
   generating a plurality of plane control signals, each of the plurality of plane control signals comprising a plane selection parameter and a plane power control parameter, wherein the plane having the plane electrode set is an inclined plane with an arbitrary angle from a vertical plane or a horizontal plane;
   receiving the plurality of plane control signals respectively through the electrode controller, selecting any plane electrode set by the electrode controller according to the plane selection parameter of the plane control signal, and then selecting a plurality of plane driving electrodes from the selected plane electrode set;
   controlling a power output ratio of any electrode in the plurality of plane driving electrodes respectively by the plane power control parameter and a first distribution condition;
   when the electrode controller drives the plurality of plane driving electrodes, using all other electrodes except the plurality of plane driving electrodes in the selected plane electrode sets to receive signals transmitted by the plurality of plane driving electrodes in order to form a set of plane voltage data; and
   performing a calculation to combine the plurality of plane control signals and the plurality of sets of plane voltage data in order to form the three dimensional electrical impedance tomographic images;
   wherein the first distribution condition is that a current distribution is performed according to the plane power control parameter, and a sum of current of the plurality of plane driving electrodes is made to be zero.

2. The three dimensional electrical impedance tomographic method of claim 1, wherein the plurality of electrodes are located on a surface of implantation body, and the implantation body is placed inside the object to be imaged.

3. The three dimensional electrical impedance tomographic method of claim 1, wherein the plurality of electrodes are located on an inner surface of a chamber, and the object to be imaged is located inside the chamber.

4. The three dimensional electrical impedance tomographic method of claim 1, wherein the plurality of electrodes are located on an inner surface of clothes, and the object to be imaged is located inside the clothes.

5. The three dimensional electrical impedance tomographic method of claim 1, wherein the plurality of electrodes are located on an inner surface of a cap or a hat, and the object to be imaged is located inside the cap or the hat.

6. The three dimensional electrical impedance tomographic method of claim 1, wherein the plane control signal is a current signal.

\* \* \* \* \*